US008468115B2

(12) United States Patent
Gartenberg

(10) Patent No.: US 8,468,115 B2
(45) Date of Patent: Jun. 18, 2013

(54) CYCLICAL BEHAVIOR MODIFICATION

(75) Inventor: Daniel Gartenberg, Fairfax, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 397 days.

(21) Appl. No.: 12/795,283

(22) Filed: Jun. 7, 2010

(65) Prior Publication Data
US 2010/0332443 A1    Dec. 30, 2010

Related U.S. Application Data

(60) Provisional application No. 61/220,472, filed on Jun. 25, 2009.

(51) Int. Cl.
*G06F 17/00*    (2006.01)
*G06N 7/04*    (2006.01)

(52) U.S. Cl.
USPC .......................................................... 706/54

(58) Field of Classification Search
USPC .......................................................... 706/54
See application file for complete search history.

(56) References Cited

U.S. PATENT DOCUMENTS

| 5,251,131 | A | * | 10/1993 | Masand et al. | 704/9 |
| 5,431,689 | A | * | 7/1995 | Weinberg et al. | 607/14 |
| 2004/0122790 | A1 | * | 6/2004 | Walker et al. | 707/1 |
| 2010/0152546 | A1 | * | 6/2010 | Behan et al. | 600/301 |

OTHER PUBLICATIONS

Teknomo, Kardi "How the K-Mean CLustering Algorithm Works" Verified by waybackj hacmine to May 2008. [ONLINE] Downloaded Aug. 23, 2012 http://web.archive.org/web/20080515215630/http://people.revoledu.com/kardi/tutorial/kMean/Algorithm.htm.*
Teknomo, Kardi (2) "Application of K-Mean Clustering" Verified by Wayback Machine to May 2008 [ONLINE] Downloaded Aug. 23, 2012 http://web.archive.org/web/20080515172426/http://people.revoledu.com/kardi/tutorial/kMean/Application.htm.*

* cited by examiner

*Primary Examiner* — Ben Rifkin
(74) *Attorney, Agent, or Firm* — David Grossman; Edgar Rodriguez

(57) ABSTRACT

Embodiments treat cyclical behaviors based on behavioral data describing physiological factors affecting the behaviors. According to various embodiments, a processor or probe produce, from the behavioral data, factor data concerning the factors. Using a processor or recommendation engine that analyzes the factor data, treatment data is recommended based on an estimate of how the at least one factor affects the at least one cyclical behavior. A processor or feedback engine determines, from the treatment data, behavioral feedback configured to produce new behavioral data and to harness the effects of the factors to improve the cyclical behaviors.

16 Claims, 25 Drawing Sheets

705

Considering only your own "feeling best" rhythm, at what time would you get up if you were entirely free to plan your day?

5:00-6:30 a.m.
    6:30-7:45 a.m.
    7:45-9:45 a.m.
    9:45-11:00 a.m.
    11:00-12:00 (noon)

Considering your only "feeling best" rhythm, at what time would you go to bed if you were entirely free to plan your evening?

8:00-9:00 p.m.
    9:00-10:15 p.m.
    10:15 p.m.-12:30 a.m.
    12:30-1:45 a.m.
    1:45-3:00 a.m.

710

Assuming normal circumstance, how easy do you find getting up in the morning?

Not at all easy
    Slightly easy
    Fairly easy
    Very easy

How alert do you feel during the first half hour after having awakened in the morning?

Not at all alert
    Slightly alert
    Fairly alert
    Very alert

During the first half hour after having awakened in the morning, how tired do you feel?

Very tired
    Fairly tired
    Fairly refreshed
    Very refreshed

You have decided to engage in some physical exercise. A friend suggests that you do this one hour twice a week and the best time for him is 7:00-8:00 a.m. Bearing in mind nothing else but your own "feeling best" rhythm, how do you think you would perform?

Would be in good form
Would be in reasonable form
Would find it difficult
Would find it very difficult At what time in the evening do you feel tired and, as a result, in need of sleep?

8:00-9:00 p.m.
9:00-10:15 p.m.
10:15 p.m.-12:30 a.m.
12:30-1:45 a.m.
1:45-3:00 a.m.

720

You wish to be at your peak performance for a test which you know is going to be mentally exhausting and lasting for two hours. You are entirely free to plan your day, and considering only your own "feeling best" rhythm, which ONE of the four testing times would you choose?

8:00-10:00 a.m.
11:00 a.m.-1:00 p.m.
3:00-5:00 p.m.
7:00-9:00 p.m.

One hears about "morning" and "evening" types of people. Which ONE of these types do you consider yourself to be?

Definitely a morning type
More morning than evening type
More evening than morning type
Definitely an evening type

FIG. 7B

How long a time does it usually take before you "recover your senses" in the morning after rising from a night's sleep?

0-10 minutes (4)
11-20 minutes ~ (3)
21-40 minutes ~ (2)
More than 40 minutes ~ (1)

During the first half hour after having awakened in the morning, how tired do you feel?

Pronounced morning active
To some extent, morning active
To some extent, evening active
Pronounced evening active

730

When would you prefer to rise (provided you have a full day's work--8 hours) if you were totally free to arrange your time?

Before 6:30 a.m.
6:30-7:30 a.m.
7:30-8:30 a.m.
8:30 a.m. or later

If you always had to rise at 6:00 a.m., what do you think it would be like?

Very difficult and unpleasant
Rather difficult and unpleasant
Unpleasant but no great problem
Easy and not unpleasant

A Modified Stanford Sleepiness Scale (SSS)™

This is a quick way to assess how alert you are feeling. Take this survey at the end of the day in order to assess how alert you felt that day.

735

| How would you describe yourself at your most alert today? | Scale Rating |
|---|---|
| Feeling active, vital, alert, or wide awake | 1 |
| Functioning at high levels, but not at peak; able to concentrate | 2 |
| Awake, but relaxed; responsive but not fully alert | 3 |
| Somewhat foggy, let down | 4 |
| Foggy; losing interest in remaining awake; slowed down | 5 |
| Sleepy, woozy, fighting sleep; prefer to lie down | 6 |
| No longer fighting sleep, sleep onset soon; having dream-like thoughts | 7 |
| Asleep | X |

| How would you describe yourself at your least alert today? | Scale Rating |
|---|---|
| Feeling active, vital, alert, or wide awake | 1 |
| Functioning at high levels, but not at peak; able to concentrate | 2 |
| Awake, but relaxed; responsive but not fully alert | 3 |
| Somewhat foggy, let down | 4 |
| Foggy; losing interest in remaining awake; slowed down | 5 |
| Sleepy, woozy, fighting sleep; prefer to lie down | 6 |
| No longer fighting sleep, sleep onset soon; having dream-like thoughts | 7 |
| Asleep | X |

745

| How would you generally describe your alertness today? | Scale Rating |
|---|---|
| Feeling active, vital, alert, or wide awake | 1 |
| Functioning at high levels, but not at peak; able to concentrate | 2 |
| Awake, but relaxed; responsive but not fully alert | 3 |
| Somewhat foggy, let down | 4 |
| Foggy; losing interest in remaining awake; slowed down | 5 |
| Sleepy, woozy, fighting sleep; prefer to lie down | 6 |
| No longer fighting sleep, sleep onset soon; having dream-like thoughts | 7 |
| Asleep | X |

905
- How do you feel today?
  1 2 3 4 5 6 7
  Sad         Happy
- Today when I thought of myself, I thought:
  1 2 3 4 5 6 7
  Negatively   Positively
- Today I thought of death:
  1 2 3 4 5 6 7
  Never       Several/day 905a — 905b — 905c 910
- How long did you do aerobic exercise today?
- How long did you do aerobic exercise today?
  1 2 3 4 5 6 7
  Not Intensely   Intensely 910a — 910b

FIG. 9A

915
- 915a: How long did you do anaerobic exercise today?
- 915b: How long did you do anaerobic exercise today? 1 2 3 4 5 6 7 Not Intensely   Intensely 920
- 920a: Were you stressed today? 1 2 3 4 5 6 7 Never   Several/day
- 920b: Today I used X medication. XXX YYY ZZZ
- 920c: Today I used X drug. XXX YYY ZZZ

How much of XXX did you eat for XXX meal?

Carbohydrates 1  2  3  4  5  6  7
None              A lot

Fat 1  2  3  4  5  6  7
None              A lot

Protein 1  2  3  4  5  6  7
None              A lot

CYCLICAL BEHAVIOR MODIFICATION

CROSS-REFERENCE TO RELATED APPLICATIONS

This application claims the benefit of U.S. Provisional Application No. 61/220,472, filed Jun. 25, 2009, which is hereby incorporated by reference in its entirety.

BRIEF DESCRIPTION OF THE SEVERAL VIEWS OF THE DRAWINGS

FIG. 7A to FIG. 7G depict an embodiment of user interfaces for collecting behavioral data concerning sleep behaviors.

FIG. 9A to FIG. 9B depict an embodiment of user interfaces for collecting behavioral data concerning depression.

FIG. 11A to FIG. 11F depict an embodiment of user interfaces for collecting behavioral data concerning behaviors affected by exercise.

DETAILED DESCRIPTION OF EMBODIMENTS

Definitions

The terms "includes," "including," "comprises" and "comprising," as used throughout this Application, should be construed to be followed with the language "without limitation," to indicate that those terms are open-ended.

The terms "a" and "an" and similar phrases are to be interpreted as "at least one" and "one or more."

The term "homeostatic factor" means the factor that pertains to the body's natural mechanisms for maintaining metabolic equilibrium, equilibrium and regulating sleep need, which is controlled by regions in the brainstem, such as the reticular formation, that serves to innervate the cortex and thereby affect arousal.

The term "circadian rhythm factor" means the factor that pertains to the body's natural energy cycle throughout a 24-hour period. The circadian component is instantiated by the interaction between hypothalamic oscillators in the suprachiasmatic nucleus of the hypothalamus and zeitbergs, such as, light. This component has a sinusoidal affect on arousal that often peaks at around 3-5 p.m. (highest arousal) and troughs at around 2-4 a.m. (lowest arousal) in a 24 hour period.

The term "sleep inertia" means grogginess that is experienced in the morning that is affected by sleep stage when awakened and that has the physiological characteristics that may include decreased cerebral blood flow. The sleep stages that affect sleep inertia include deep sleep, rapid-eye movement and light sleep.

The term "cyclical" means having a regular, or periodic, effect. The period could be a 24-hour period, or some other length period.

Data Processing System

Figure 1:
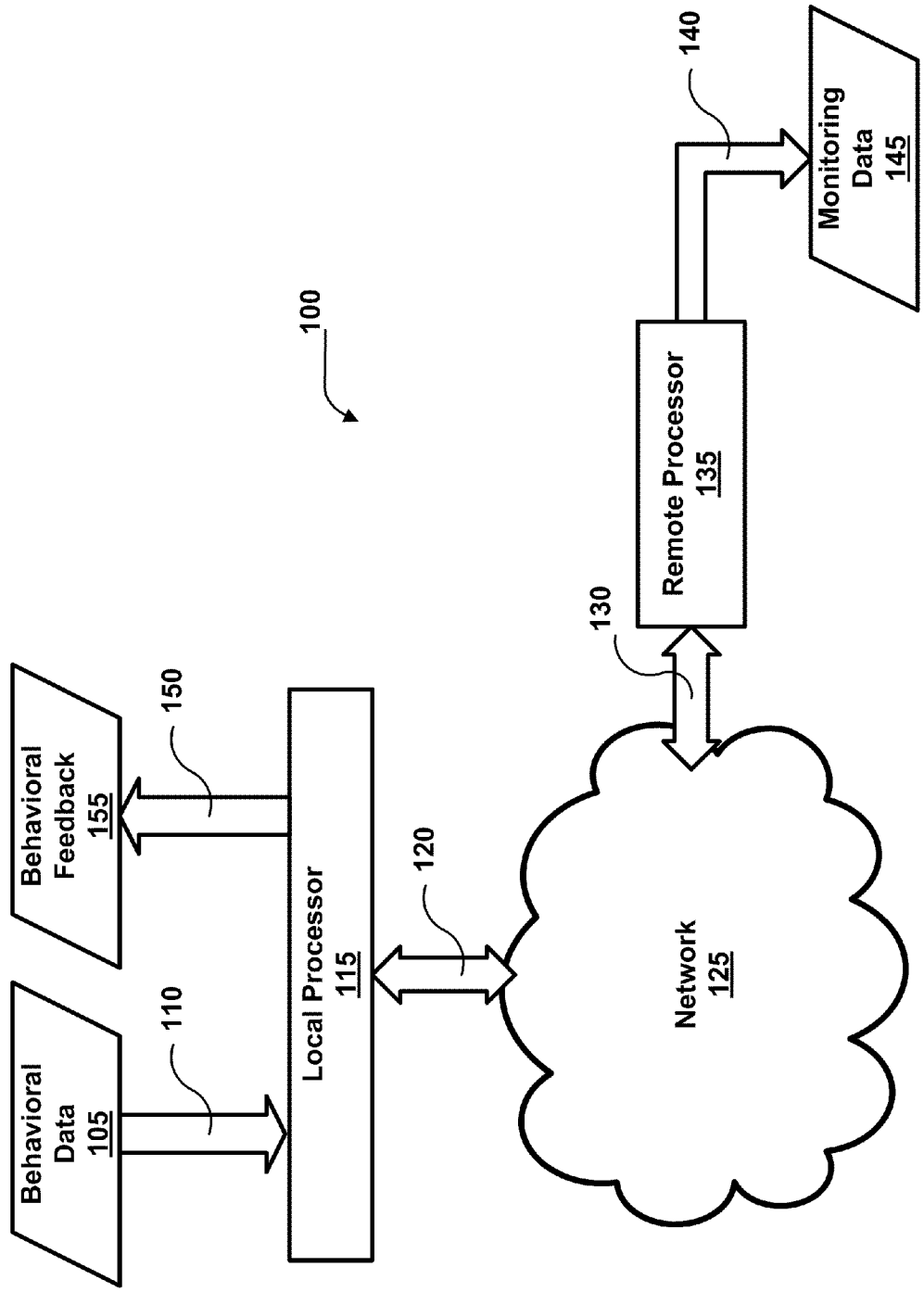
FIG. 1 depicts an embodiment of a data processing system for treating cyclical behaviors.

FIG. 1 depicts an embodiment of a data processing system 100. Data processing system 100 may be configured to analyze behaviors based on behavioral data and recommend a treatment through behavioral feedback. Because the behaviors of interest are affected by physiological factors that have a recurring—or, cyclical—effect on the behaviors, the behaviors of interest are referred to herein as "cyclical behaviors." Some cyclical behaviors may include those related to sleep, depression, fitness or any combination thereof. Of course, many other behaviors may be treated by system 100. For instance, any behavior sensitive to cyclical factors, such as drug relapses, psychotic disorders, physiological disorders, medication dosages, ability to learn, personality traits, creativity, analytical thinking and/or any combination thereof. System 100 may probe a user for the behavioral data by issuing behavior-specific surveys, behavior-specific feedback or any combination thereof. The behavioral feedback may be configured to improve the user's behavior. The feedback may also be configured to include multiple instances of feedback across a sampling window of variable size. Consequently, system 100 may estimate the effects of a factor on a cyclical behavior by observing how a random variable, correlated with the factor, affects the cyclical behavior. The estimated effects may form the basis for a recommended treatment that improves the cyclical behavior by harnessing the effects of the factor on the cyclical behavior. For example, a treatment may include a recommendation configured to induce a user to behave in a way that minimizes the effect of a factor determined to negatively affect a cyclical behavior. On the other hand, treatment may include a recommendation configured to maximize the effect of a factor determined to positively affect a cyclical behavior. The recommended treatment may then be used by system 100 to update the behavioral feedback used in a future probe, such that the user's behavior is improved. The updated feedback may also form part of a newly defined sampling window that system 100 may use to refine future iterations of feedback.

System 100 may capture behavioral data 105 and output behavioral feedback 155. The content and form of both behavioral data 105 and behavioral feedback 155 depends on the particular cyclical behavior that system 100 is intended to treat at a given time. Examples of content for behavioral data 105 include user responses to various surveys (e.g., behavioral, habits, sleep, depression, fitness or any combination thereof), scores from various tests (e.g., vigilance, cognitive, fitness or any combination thereof), motion data, physiological measurements, user preferences/instructions, cyclical behavior selections, billing history from electronic payments or any combination thereof. On the other hand, the content of behavioral feedback 155 may include user instructions, alarms, appliance instructions or any combination thereof. Moreover, the form of behavioral feedback may correspond to the content of the feedback. For instance, user instructions may be visual, audible or any combination thereof. Alarms may be visual, audible, thermal, tactile, optical, olfactory or any combination thereof. Appliance instructions may be in a machine-readable format, such as electrical, optical or any combination thereof. These instructions may be used to direct the machine behavior.

System 100 may capture behavioral data 105 through the facility of input means 110. Input means 110 may include at least one form of user input and at least one communications medium. For instance, user input may include touch screens, switches, keyboards, microphones, motion sensors, physiological sensors or any combination thereof. The communications medium may include electrical, optical, acoustic, mechanical, wireless mediums or any combination thereof for communicating behavioral data 105.

A local processor 115 may provide local processing of data, including behavioral data 105, behavioral feedback 155 or any combination thereof. Further, local processor 115, in combination with input means 110 and communications means 120, may interface with users, remote devices or any combination thereof. The local processing provided by local processor 115 includes receiving behavioral data 105; processing data for transmission using communications means 120; processing data received from communications means 120; producing behavioral feedback 155; issuing behavioral feedback 155 or any combination thereof. Local processor 115 may take on numerous forms, including mobile phones, media devices, personal digital assistants, laptop and notebook computers, desktop computers, alarm clocks, pagers, other electronic devices or any combination thereof.

Communication means 120 may facilitate communication between local processor 115 and a network 125 that interconnects communications means 120 with a second communications means 130, similar to the means 120, and a remote processor 135. Further, communication means 120 and 130 may include a communications medium and a transceiver appropriate for communicating over the communications medium. The communications mediums of communications means 120 and 130 and network 125 may include mediums and networks that are electrical, optical, acoustical, mechanical, wired, wireless or any combination thereof for communicating data. The network 125 may accordingly be a wide area network including the Internet, a local area network, a personal network using Bluetooth or any combination thereof.

Remote processor 135 may operate on data received over network 125 to produce various outputs. For example, remote processor 135 produces, through monitoring means 140, monitoring data 145 concerning the behavioral data 105. Monitoring data 145 may include a history of a cyclical behavior as reflected by behavioral data 105. By producing monitoring data 145 in the form of a history, the cyclical behavior of a user may be evaluated to produce a professional assessment of the behavior, a diagnosis of a physiological or psychological disorder, the health of a user or any combination thereof. Although monitoring means 140 is depicted as being coupled to remote processor 135, it may be coupled to local processor 115.

In addition to monitoring data 145, remote processor 135 may produce information for reproduction over output means 150. Such information from remote processor 135 may include behavioral feedback 155, generated according to behavioral data 105. Like local processor 115, remote processor 135 may take on various forms, including servers, databases, network hosts, mobile phones, media devices, personal digital assistants, laptop and notebook computers, desktop computers, pagers, other electronic devices or any combination thereof.

Monitoring means 140 and output means 150 may be output devices whose form depends on the content of information to be conveyed. Forms of means 140 and 150 may include visual, audible, thermal, tactile, optical, olfactory or any combination thereof. For example, the output means may include visual displays, loudspeakers, vibratory alarms, toasters, coffee makers, household lights, other devices capable of producing a stimulus or any combination thereof.

The various components of system 100 set forth in the foregoing are merely examples. For instance, one may embody system 100 without monitoring means 140. All processing of system 100, such as the analysis of behavioral data 105 and the production of both the behavioral feedback 155 and the monitoring data 145, may be localized to local processor 115. In another example, behavioral data 105 is transmitted to remote processor 135 without local processor 115. Alternatively, output means 150 outputs behavioral feedback 155 directly from network 125 or from remote processor 135. Other modifications are contemplated, as would be appreciated by one skilled in the art.

Figure 2:
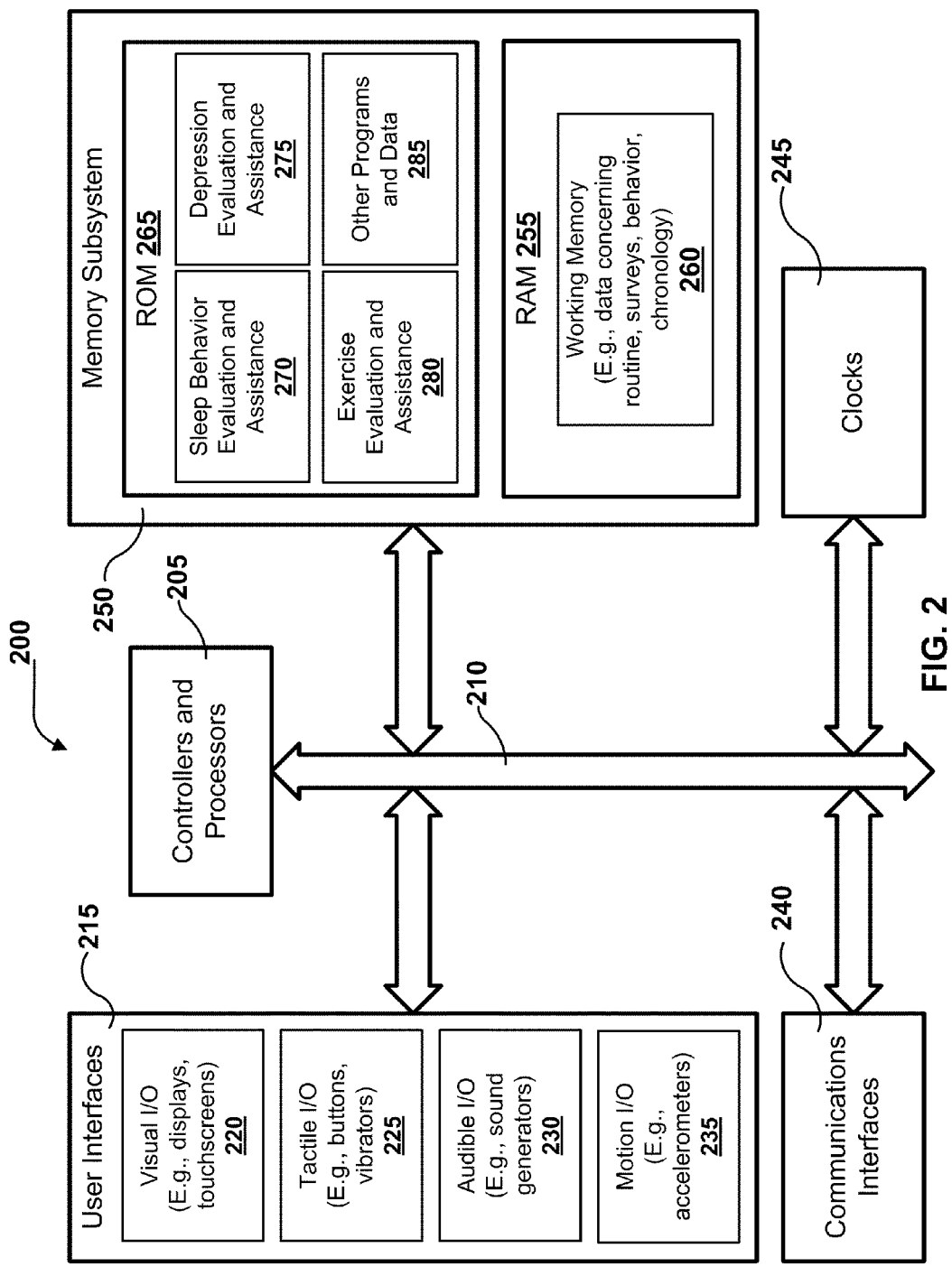
FIG. 2 depicts an embodiment of a data processor for use in the data processing system of FIG. 1.

FIG. 2 depicts an embodiment of a data processor 200 that may be used in data processing system 100. In particular, the data processor 200 may embody local processor 115 and/or remote processor 135. Data processor 200 may include controllers and processors 205 that control the components of data processor 200, execute program instructions, and process data within data processor 200. The controllers and processors 205 may include microprocessors, microcontrollers, systems-on-a-chip, field-programmable gate arrays, application specific integrated circuits or any combination thereof. To facilitate the operation of the controllers and processors, data processor 200 may include a bus 210 for interconnecting the controllers and processors 205 with user interfaces 215, communication interfaces 240, clocks 245 and memory subsystem 250.

As suggested by the foregoing description of the forms of behavioral data 105 and behavioral feedback 155, user interfaces 215 may include a combination of various components for capturing and reproducing data. In general, user interfaces 215 implement the input means 110 and output means 140 and 150. Depicted in FIG. 2 are four potential I/O components. First, a visual I/O component 220 may provide displays, touch screens or any combination thereof for providing the visual depiction and capturing of data. Second, a tactile I/O component 225 may include buttons, switches, vibratory mechanisms and/or any combination thereof to depict and capture data. Third, an audible I/O component 230 may include microphones, sound generators, speakers, headphones or any combination thereof to acoustically depict and capture data. Finally, a motion I/O component 235, like an accelerometer, may provide for the capture of data related to the motion of a user. These four components are not an exclusive listing of all the I/O components conceived as usable in the data processor 200. For instance, user interfaces 215 may include I/O components for directly capturing physiological measurements, like heart rate, sleep state or any combination thereof. Another possible I/O component is an I/O component for communicating with household electronics, like kitchen appliances, toasters, coffee makers, household lighting or any combination thereof. In connection with a household electronics I/O component, data processor 200 may control household electronics according to behavioral feedback 155.

Communications interfaces 240 may provide all communication between local data processor 200 and an external processor. In general, communications interfaces 240 may embody the communications means 120 and 130.

Clocks 245 represent the system clocks that may be used by data processor 200 for various processing tasks. In an alarm setting, clocks 245 may provide time triggers, indicating when to issue an alarm through user interfaces 215. In a communication setting, clocks may facilitate the synchronization of data transmission and reception. For general processing of data, clocks 245 may synchronize controllers and processors 205 as well as the other components of system 200.

Memory subsystem 250 may comprise various components, including RAM 255 and ROM 265. RAM 255 may be a volatile memory source usable as working memory for the general processing of data within data processor 200. For example, RAM 255 may include flash, solid-state memory, floppy disks, optical disks, hard disks or any combination thereof. The data stored within RAM 255 depends on the program being executed by processors 205. As illustrated in FIG. 2, RAM 255 stores behavioral data 105 being analyzed by processors 205 to produce behavioral feedback 155. ROM 265 may be a nonvolatile memory source storing programs 270, 275, 280 and 285. Embodiments of ROM 265 may include storage devices, like hard disks, floppy disks, optical disks, removable media, flash media, hardware registers, solid-state memory or any combination thereof. The programs 270, 275, 280 and 285 may alternatively be provided through other media besides ROM 265, such as instructions modulated on a carrier wave and transmitted over wired, wireless channels or any combination thereof.

Programs 270, 275, 280 and 285 may encode instructions for causing processors 205 to execute different processes. Programs 270, 275 and 280 represent three processes for producing behavioral feedback 155 to treat cyclical behaviors. Specifically, program 270 may encode instructions for treating sleep behaviors, program 275 may encode instructions for treating depression and program 280 may encode instructions for treating fitness behaviors. Program 285, on the other hand, may include operating systems, drivers, other applications or any combination thereof. As an alternative to executing programs 270, 275, 280 and 285, controllers and processor 205 may be embodied as hardware.

As local processor 115 and remote processor 135 are optional, at least some components of data processor 200 may be eliminated depending on whether system 100 includes local processor 115, remote processor 135 or both. For instance, remote processor 135 may be embodied without user interfaces 215. Programs 270, 275 and 280 may be embodied in the local processor 115, remote processor 135 or both. Where local processor 115 performs all processing, one may forego communications interfaces 240. Other modifications are contemplated and would be apparent to those of skill in the art.

Behavior Treating System

Figure 3:
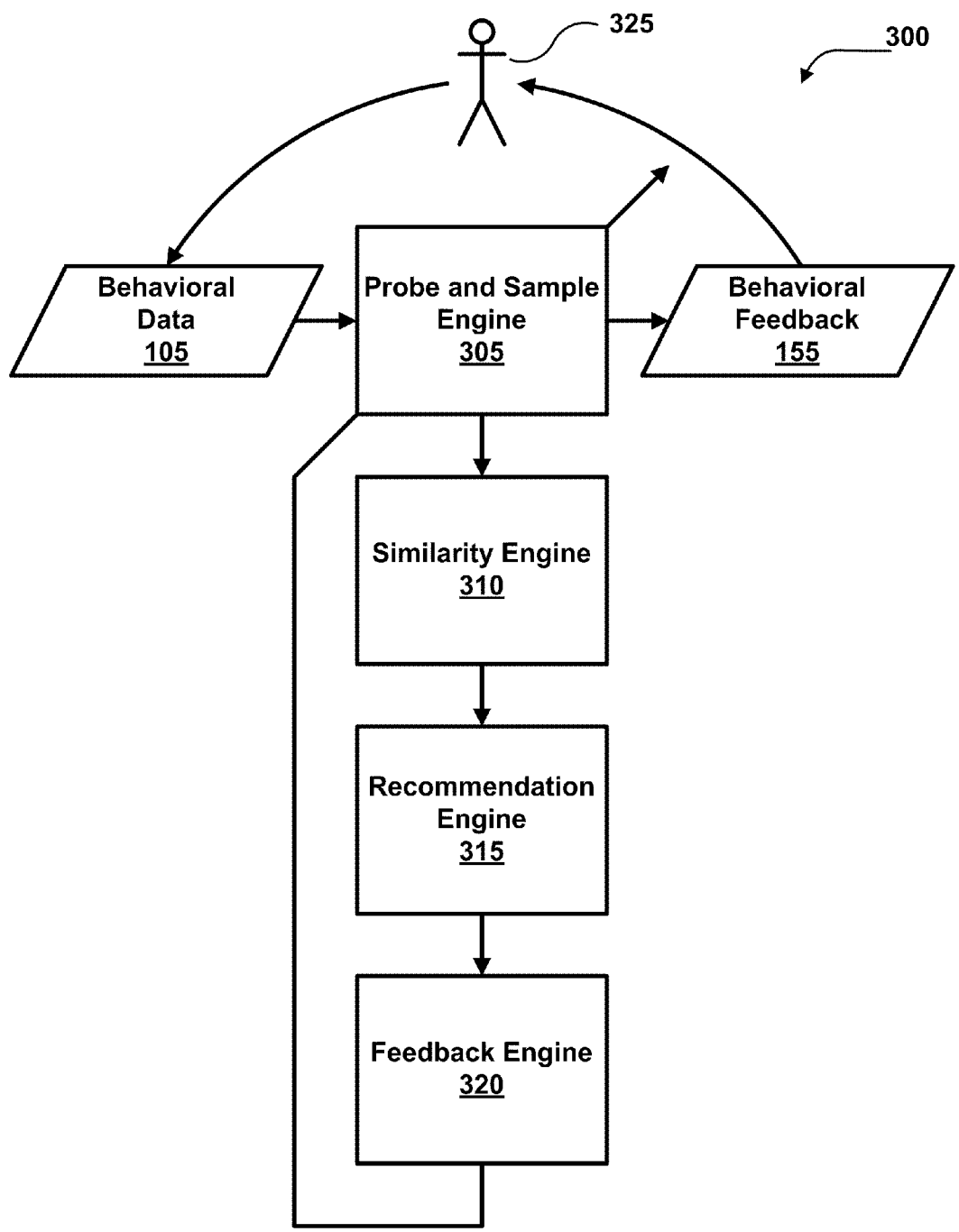
FIG. 3 depicts an embodiment of a behavioral treatment system.

FIG. 3 depicts an embodiment of a behavior treating system 300. Behavior treating system 300 may include four engines configured to treat cyclical behaviors. The probe and sample engine 305 may obtain behavioral data 105 from user 325 and then execute actions to produce behavioral feedback 155. Engine 305 may also receive updated behavioral data 105 based on the behavioral feedback 155. Moreover, engine 305 may produce samples from the behavioral data 105. The similarity engine 310 may receive the samples output from engine 305 and execute an action to produce a list of quantitatively similar samples. The recommendation engine 315 may analyze the list of samples output from engine 310 and execute a subsequent action to recommend a treatment. The feedback engine 320 may execute further actions to update engine 305 based on the recommended treatment output by engine 315. In this way, the engines may produce behavioral feedback 155 based on behavioral data 105, and the feedback 155 may be updated over time to converge towards an optimal treatment for a cyclical behavior. The engines may be discrete hardware components, software executing on at least one computer or any combination thereof. For example, all four engines could be embodied by a single instance of data processor 200. Alternatively, the engines could be embodied by at least two instances of data processor 200 that are connected in a system similar to system 100.

System Operation

Figure 4:
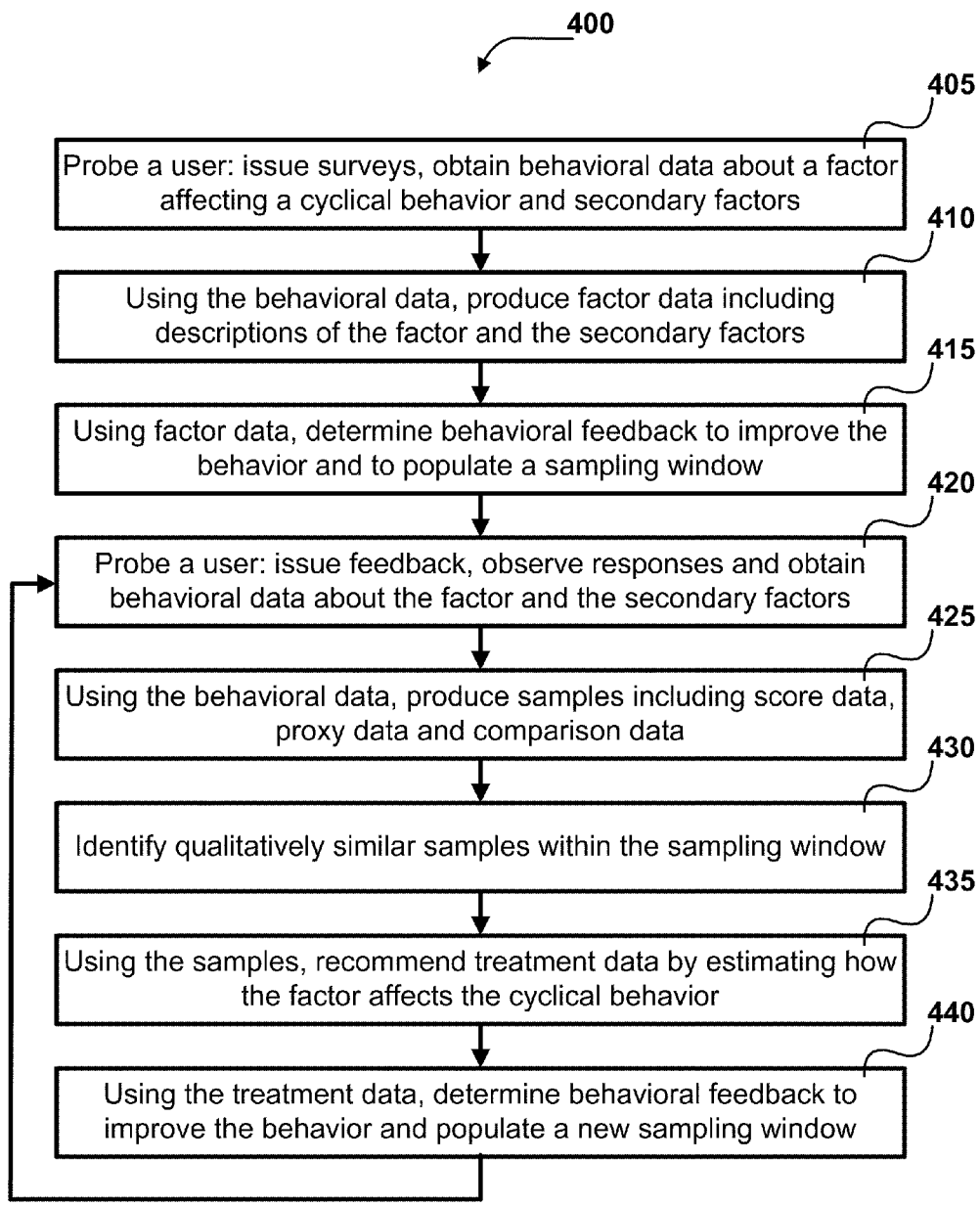
FIG. 4 depicts an embodiment of actions executable by the systems of FIG. 1 and FIG. 3 for treating cyclical behaviors.

One embodiment of the operation of system 100 and system 300 is depicted in FIG. 4. Specifically, system 100 may begin by probing a user according to action 405 to collect an initial set of behavioral data 105 through input means 110. The action 405 of probing a user may include issuing surveys from local processor 115 or remote processor 135, reproducing the surveys over output means 150, receiving user responses over input means 110 or any combination thereof. Alternatively, action 405 may be executed by probe and sample engine 305. Answers to the surveys may enable processor 115/135 or engine 305 to produce an initial description of factors suspected to be affecting a cyclical behavior as well as initial descriptions of any secondary factors that may also be affecting the cyclical behavior. For example, the surveys may include questions whose answers enable a quantitative description and/or a quantitative description, like the time of the trough of a user's circadian rhythm, whether someone is suffering sleep deprivation, age, weight, gender or any combination thereof. These determined descriptions are referred to herein as "factor data."

Either local processor 115 or remote processor 135 may use the initial behavioral data 105 to produce the factor data according to action 410. Alternatively, action 410 may be executed by probe and sample engine 305. The process of determining factor data may include extrapolating a description directly from a survey, combining multiple survey answers over time to produce an estimate description or any combination thereof. Descriptions of factors and secondary factors may be essentially the same. For example, determining whether someone is sleep deprived may include analyzing bed time and wake time across several days to determine that a user is not getting enough sleep. More examples are described in the following sections.

Using the factor data, local processor 115, remote processor 135 or engine 320 performs action 415 to determine behavioral feedback 155. Behavioral feedback 155 may be configured in action 415 to recommend an initial treatment for improving a cyclical behavior. For example, recommendations may include suggesting a time to wake-up, an alarm time, an exercise amount or any combination thereof. Moreover, behavioral feedback may include multiple instances of behavioral feedback that are to be issued and reproduced during a sampling phase, such that the feedback and associated user responses may be plotted as samples that populate a sampling window. For instance, the multiple instances of behavioral feedback may be selected to test a user response at various values, across the sampling window, of a random variable correlated with a factor affecting a cyclical behavior. By determining multiple instances of behavioral feedback across a sampling window, one processor 115/135 or engine 315 may evaluate the effects of a random variable on a cyclical behavior. Moreover, when this random variable is correlated with a factor that affects the cyclical behavior, processor 115/135 or engine 315 may estimate the effects of the factor on the cyclical behavior. This estimate may then form a basis for treating the behavior by harnessing the effects of the factor.

Action 420 may be executed by local processor 115, remote processor 135 or engine 305. The action may include issuing the behavioral feedback determined in action 415 as behavioral feedback 155. Action 420 may also operate on an updated set of behavioral feedback 155 determined according to step 440, which is described below. In addition, action 420 may include issuing surveys to monitor changes in initial data and tests to monitor how variations in the multiple instances of feedback are affecting a cyclical behavior. Any issued feedback, survey or test may be reproduced by output means 150 or engine 305. Action 420 may likewise include using input means 110 or engine 305 to observe user responses to the feedback, surveys and tests to obtain updated behavioral data 105.

Local processor 115, remote processor 135 or engine 305 may analyze, in action 425, the data obtained in action 420 and produce samples of updated factor data. The samples produced in action 425 may include factor data that may take into account user responses that include survey answers and test scores. Accordingly, processor 115/135 or engine 305 may produce samples with comparison data, which may include updated descriptions of secondary factors. Further, processor 115/135 or engine 305 may plot, in a sampling window, test scores against a random variable correlated with a factor affecting a cyclical behavior. The values of the random variable may be represented in the samples as proxy data, so-called because the random variable is correlated with a factor affecting a cyclical behavior, such that variations in the random variable may act as a proxy to variations in the factor. Using proxy data enables systems 100 and 300 to monitor the effects of a factor when the relationship between the factor and its effects on a cyclical behavioral cannot be assessed directly from behavioral data 105.

Action 430 may be executed by local processor 115, remote processor 135 or engine 310. The action may include analyzing the samples produced in action 425 to determine which samples are quantitatively similar. This similarity processing may include comparing the comparison data of samples within a sampling window. In this way, systems 100 and 300 may calculate on a factor-wise basis, the distance between the descriptions of a set of secondary factors of a first sample and the descriptions of a set of secondary factors of a second sample. Action 430 may further include comparing each factor-wise distance against a factor-specific threshold to determine whether the samples are quantitatively similar. For instance, if each distance is smaller than the threshold, then the samples may be declared similar.

The factor-specific thresholds used in action 430 may be predetermined by processor 115/135 or engine 310 of system 300. Alternatively, systems 100 and 300 may adapt the thresholds in consideration of any intra-personal relationship between a secondary factor and its effect on a cyclical behavior. For instance, a threshold may vary proportionately with the degree of dependence between sampled test scores and the particular secondary factor. Thus, based on a multiple regression analysis between secondary factor descriptions (the independent variable) and sampled test scores (the dependent variable), secondary factors exhibiting large beta weights may have proportionally reduced similarity thresholds.

Another type of intra-personal analysis may determine whether samples are quantitatively similar by eliminating, from the set of secondary factors, any secondary factors that have a negligible effect on a user's scores. For instance, if a secondary factor exhibits a small beta weight, that factor may be assumed to have no statistical relevance to the similarity between samples. Accordingly, systems 100 and 300 may ignore that factor in determining quantitatively similar samples. The threshold between beta weights that have statistical significance and those that do not may be predetermined, or may vary based on further intra-personal analysis. For instance, if an analysis of sampled scores reveals that the scores exhibit low variance based on comparison to a predetermined variance threshold, the threshold between statistical significance and insignificance may be appropriately reduced.

Based on any samples identified as quantitatively similar, systems 100 and 300 may recommend, in action 435, treatment data. In general, local processor 115, remote processor 135 or engine 315 may recommend treatment data that will encourage a user to behave in a more desirable manner. The recommended treatment data may be based on an estimate of how a factor is affecting a cyclical behavior. The estimation of how a factor is affecting a cyclical behavior may include analyzing the relationship between sampled scores and the proxy data describing the values of a random variable correlated with the factor. As described in connection with action 425, processor 115/135 or engine 305 may plot the relationship between sampled scores and proxy data taken across a sampling window of variable size. Action 435 may consequently analyze the relationship between sampled scores and proxy data by identifying any samples associated with the most desirable effect within the sampling window. For instance, action 435 may select, for use as a treatment sample, a sample plotted within the sampling window and associated with the highest score. By selecting the highest score, action 435 may emphasize the positive effects of a factor to treat a cyclical behavior. On the other hand, selecting a lowest score may diminish the influence of a negative factor on a cyclical behavior.

As an alternative to selecting a single sample, systems 100 and 300 may select a block of samples from within a sampling window. First, local processor 115, remote processor 135 or engine 315 may divide the sampling window into blocks, and arrange any quantitatively similar samples into the blocks based on the proxy data of the quantitatively similar samples. Each block may contain at least one quantitatively similar sample. Second, the score data of each quantitatively similar sample is combined in each block to produce at least one combined score for each block. The combination may be an average, an aggregate, other statistical combination or any combination thereof. From among the combined scores, processor 115/135 or engine 315 may identify at least one block that has a score that is a local extreme, such as a local maximum or local minimum. The local extreme in question may depend on whether the treatment recommendation is seeking to maximize or minimize the effect of a factor affecting a cyclical behavior.

In one embodiment, systems 100 and 300 may analyze the effect of factors on two or more cyclical behaviors. In that case, action 435 may further include processor 115/135 or engine 315 weighting scores in each block according to the behavior to which the scores pertain. For instance, a user may specify a degree of relative importance between a first behavior and a second behavior. In that case, processor 115/135 or engine 315 may optimize a recommended treatment by weighting normalized scores of the first behavior according to its relative importance and weighting the normalized scores of the second behavior according to its relative importance. The weighted scores for each behavior may then be combined into a weighted combination of score data that is analyzed to identify a local extreme within a sampling window. The sample or block containing the local extreme will be selected as the treatment sample block for use in action 440.

Regardless if the treatment sample includes a single sample or a block of samples, the treatment sample may be used by local processor 115, remote processor 135 or engine 320 to execute action 440. Action 440 may include deriving new feedback, a new sampling window or any combination thereof. Processor 115/135 or engine 305 in combination with engine 320 uses the output of action 440 to update the feedback issued in action 420. For example, action 440 may include producing feedback according to the proxy data of the treatment sample. Thus, if a treatment sample has proxy data indicating an alarm time of 8:00 AM, executing action 440 may produce feedback including an alarm time of 8:00 AM. If the treatment sample includes a block of samples associated with a range of values of a random variable, executing action 340 may produce multiple instances of feedback within a new sampling window that is substantially equal in size to the range of values. Alternatively, if systems 100 or 300 are evaluating the effects of more than one factor on a cyclical behavior, action 440 may produce feedback in an entirely different sampling window.

Since a cyclical behavior may be affected by more than one factor for which systems 100 and 300 determine factor quantities, the behavioral feedback produced by local processor 115, remote processor 135 or feedback engine 320 may similarly take into account more than one factor. Where the systems consider more than one factor in producing behavioral feedback, processor 115/135 or engine 320 may consider factors in a hierarchical manner, producing feedback based on a first factor only if a second factor is not currently co-varying with the cyclical behavior. Alternatively, the systems may produce feedback by linearly combining factors, where the weights applied to each factor are determined by a Likert scale indicating the importance of a factor.

It should be noted that systems 100 and 300 illustrate embodiments of systems for treating cyclical behaviors according to process 400. The illustrated components may be eliminated or configured in multiple embodiments. For example, where local processor 115 acts alone, all foregoing actions of process 530 may occur within processor 115 without the intervention of components 120, 125, 130 or 135. On the other hand, where remote processor 135 acts alone, all foregoing processing step may occur within processor 135 with processor 115 merely serving to pass data to/from remote processor 135, input means 110 and output means 150. Communication means 120 may pass behavioral data to network 125, network 125 may pass the behavioral data to communication means 130 and means 130 may pass the behavioral data to remote processor 135. The behavioral feedback 155 may accordingly passed back from remote processor 135 to output means 150 through communication means 130, network 125, communication means 120 and/or local processor 115. The engines of system 300 may be embodied together in a single device or in a system of interconnected devices.

The foregoing description set forth one embodiment for treating cyclical behaviors. The following sections set forth examples concerning specific forms of cyclical behavior: sleep, depression and fitness. Of course, other forms of behavior are susceptible to treatment by the data processing system set forth in this section. For instance, systems 100 and 300 may be configured to treat susceptibility to drug relapses, psychotic disorders, physiological disorders, medication dosages, ability to learn, personality traits, creativity, analytical thinking and/or any combination thereof.

Treating Sleep Behaviors

Figure 5:
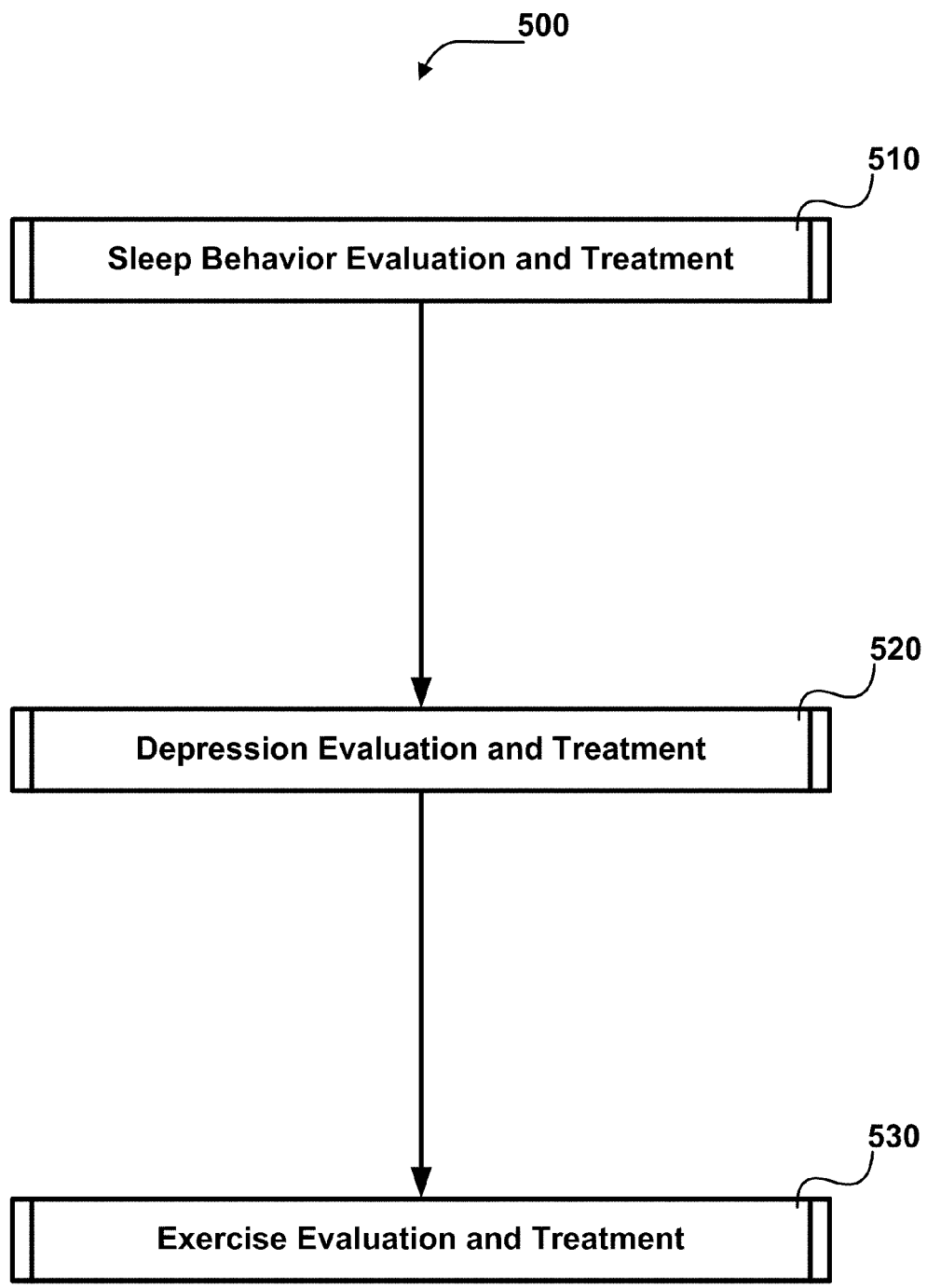
FIG. 5 depicts an embodiment of actions executable by the systems of FIG. 1 and FIG. 3 for treating sleep behaviors, depression and behaviors affected by exercise.
Figure 6:
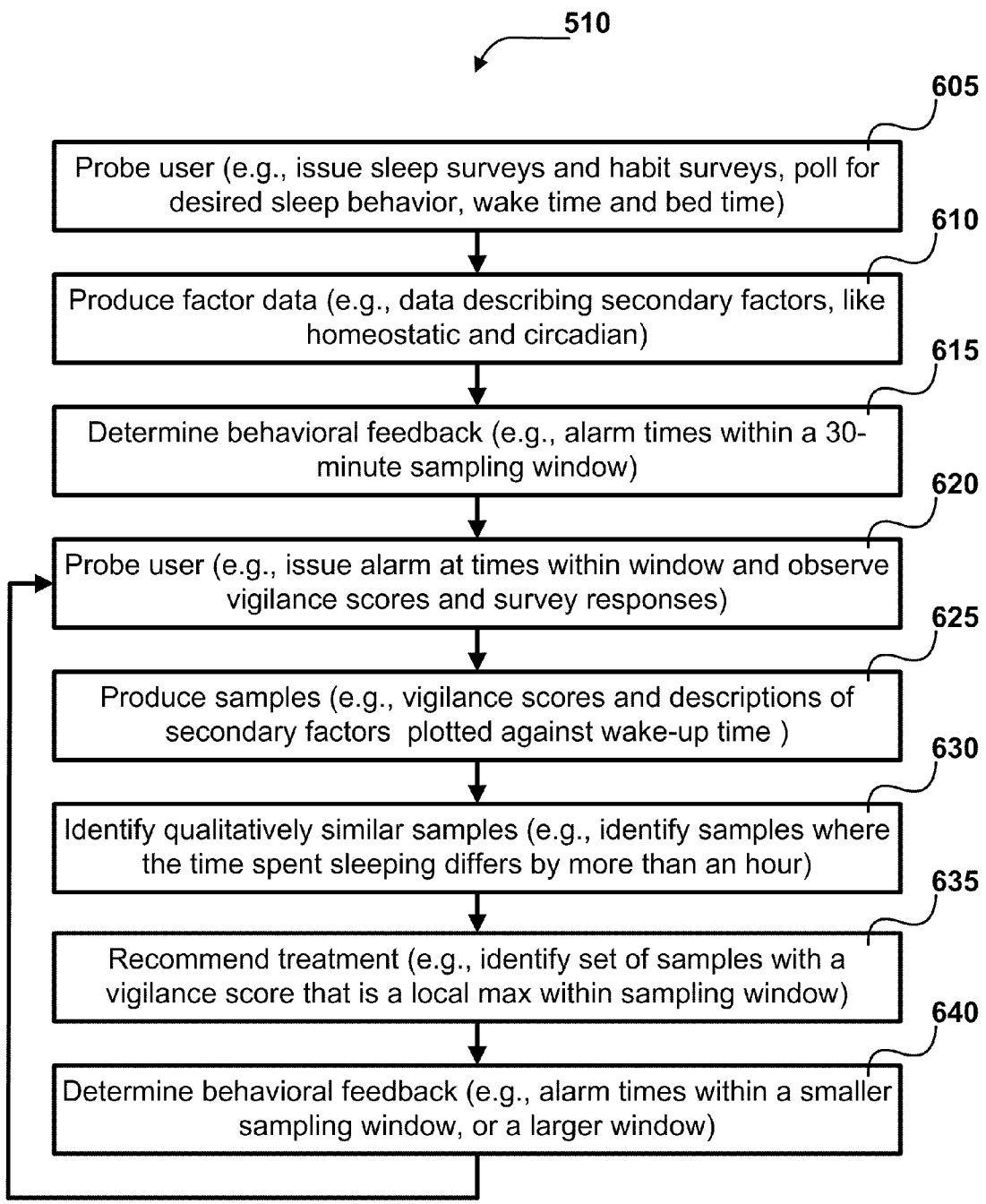
FIG. 6 depicts an embodiment of actions for treating sleep behaviors according to FIG. 5.

As depicted in FIG. 5, systems 100 and 300 may be configured to perform a cyclical behavior treatment process 500. For instance, system 100 and 300 may be configured to execute process 500 in accordance with programs 270 to 285. One portion of cyclical behavior treatment process 500 may include a sleep behavior evaluation and treatment process 510 according to program 270. FIG. 6 depicts an example of process 510 for treating sleep inertia severity. In brief, process 510 may include systems 100 or 300 obtaining data so it may produce measurements of how sleep stage when awakened affects sleep inertia severity and descriptions of secondary factors that affect sleep inertia. The secondary descriptions may enable systems 100 or 300 to isolate the effects of at least one factor on sleep inertia severity, such that the system may estimate the effects of the factor and recommend a treatment that harnesses the effects of the factor. Specifically, systems 100 or 300 may determine secondary descriptions of a user's circadian rhythm component and homeostatic component and then use those descriptions to isolate and estimate the effects of sleep-stage when awakened on sleep inertia severity. System 100 then produces behavioral feedback that harnesses the effects of sleep-stage when awakened to reduce sleep inertia severity.

The actions of process 510 are similar to the actions depicted in FIG. 4. Action 605 may include using input means 110 and output means 150 to probe a user for initial behavioral data 105. Alternatively, action 605 uses probe and sample engine 305. Initial behavioral data 105 in the sleep inertia context may include answers to sleep surveys and answers to habits surveys. Some interfaces for collecting this initial data are described below in connection with FIG. 7A to FIG. 7E.

After capturing initial behavioral data 105 in action 605, local processor 115, remote processor 135 or probe and sample engine 305 may process the initial data in action 610 to produce factor data describing, at least, circadian and homeostatic factors. For instance, the circadian factor may be quantified as the time of day at which a user experiences a trough or crest in his circadian rhythm. The homeostatic factor may be quantified as a sleep-duration or a wake-duration based on survey answers indicating when a user went to bed and when a user woke up. Other data produced in action 610 includes a desired wake-up time.

In action 615, local processor 115, remote processor 135 or feedback engine 320 may use the factor descriptions from action 610 to determine appropriate behavioral feedback. For instance, when the cyclical behavior of interest is a reduction in sleep inertia severity, and a user has entered a desired wake-up time, processors 115/135 or engine 320 may produce feedback that provides a proxy indication of how sleep stage when awakened affects sleep inertia severity. The proxy may be a random variable that is correlated to sleep stage when awakened. Thus, the behavioral feedback may be a set of alarms set to wake a user up at different times. In this context, the behavioral feedback may include many instances of behavioral feedback, such that processors 115/135 or engine 305 may produce samples indicating how different alarm times affect sleep inertia severity. For example, processors 115/135 or engine 305 may determine five instances of alarm times within a 30-minute window.

Figure 7F:
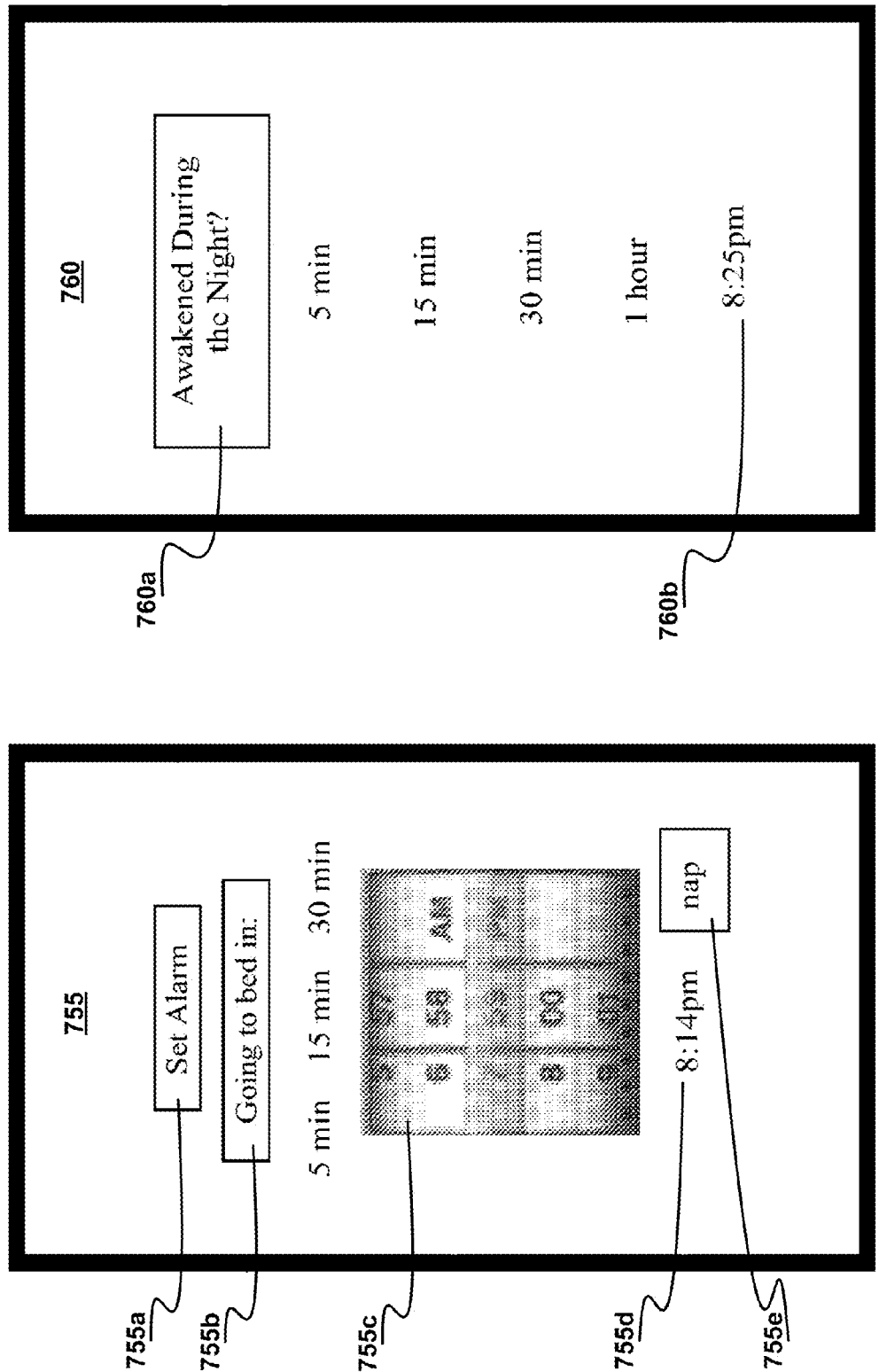
Figure 7G:
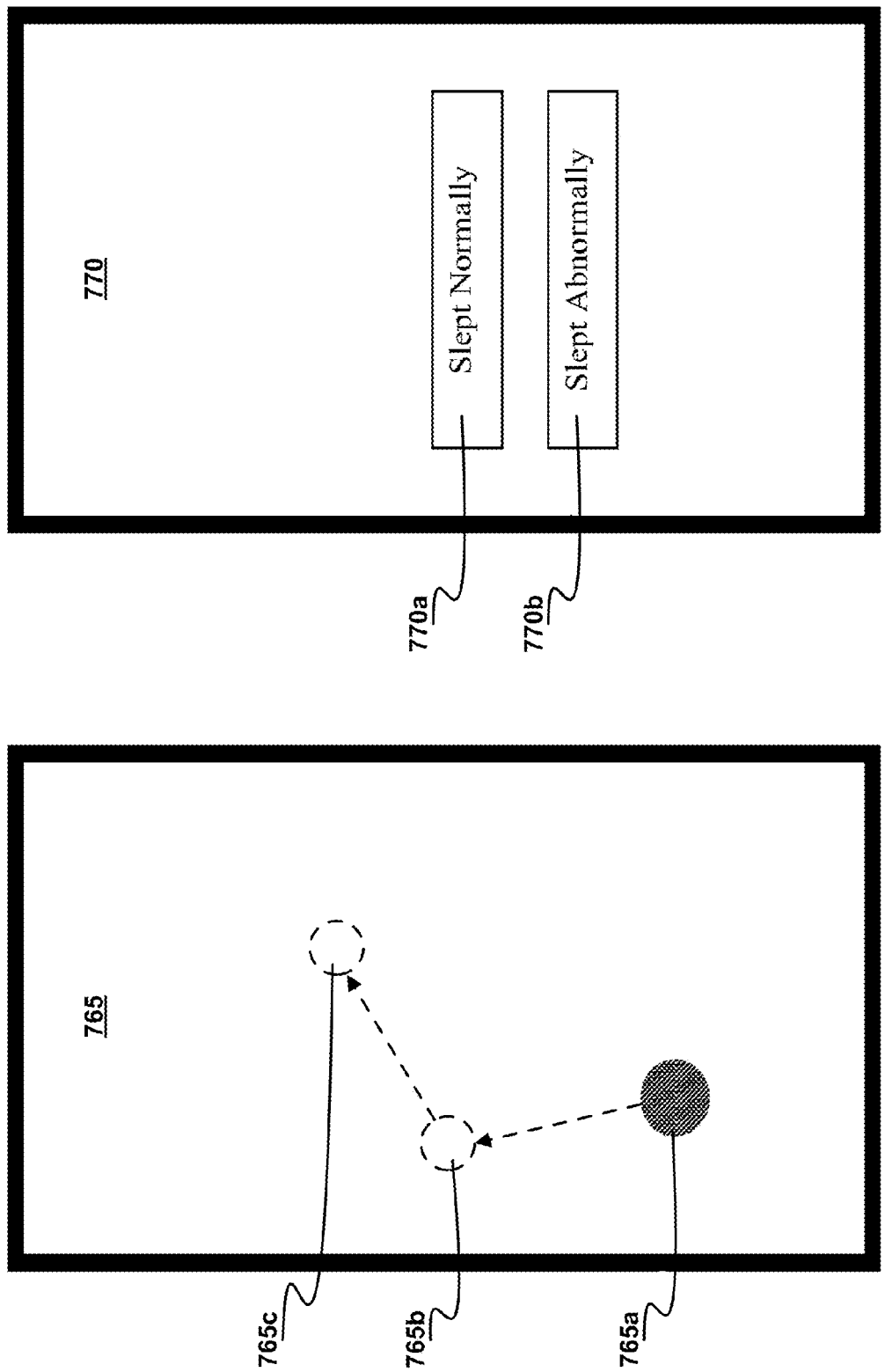

Action 620 may include using input means 110, output means 150 or probe and sample engine 305 to issue further user surveys, tests and the behavioral feedback 155 determined in action 615. Of course, act 620 may also include issuing feedback based on the behavioral feedback determined according to act 640. FIG. 7F and FIG. 7G, described below, depict interfaces for issuing surveys and tests. The surveys and tests may be issued upon waking in the case of reducing sleep inertia, or throughout the day depending on whether the data concerns behavior immediately upon waking, behavior throughout the day or behavior immediately preceding sleep. As set forth in the description of FIG. 1, if behavioral feedback is an alarm, the alarm may include alarm components of various forms, including light, sound or any combination thereof. Alternatively, systems 100 or 300 may produce an alarm by controlling household electronics. Starting the coffee maker may provide olfactory stimulus, opening blinds or turning on lights may provide light stimulus, turning on a TV or radio may provide audio stimulus, etc. Where the behavioral feedback produced in action 615 includes many instances of feedback, action 620 may include reproducing the instances in a random order until all instances of the feedback are issued at least once.

In addition to issuing surveys and feedback, action 620 may include local processor 115, remote processor 135 or probe and sample engine 305 monitoring for user responses and obtaining data related to the responses. User responses to surveys may include a new desired wake-up time, indications of sleepiness, bed time, whether the user took a nap, if the user's sleep was interrupted, whether the user's sleep was abnormal, time of sleep onset or any combination thereof. Moreover, user responses may include score data including test scores indicating a user's vigilance, cognitive abilities upon waking or any combination thereof. The output means 150 may reproduce each instance of feedback 155 continuously or repeatedly until a user responds to the feedback by completing a test that is associated with that instance of feedback.

Action 625 may include local processor 115, remote processor 135 or probe and sample engine 305 producing samples of factor data based on the user responses obtained in action 620. The factor data includes descriptions of secondary factors, excluding sleep stage when awakened. For instance, descriptions of the homeostatic component may include the time spent awake or the time spent sleeping before a user response was sampled. Descriptions of the circadian component may include the time of day when a user response was sampled. These secondary factor descriptions may be used in action 630 to identify similar samples, so these descriptions are referred to as "comparison data." In addition to comparison data, each sample produced during action 625 may include score data that describes a vigilance/cognitive test score and proxy data indicating the wake-up time associated with a particular test score. The score data and proxy data may enable system 100 to plot test scores versus wake-up times.

Using the samples from action 625, local processor 115, remote processor 135 or similarity engine 310 may identify any samples that are quantitatively similar in action 630. In the sleep inertia context, action 630 may include identifying quantitatively similar samples by comparing comparison data for the circadian rhythm and homeostasis. For instance, if samples describe the homeostatic component of sleep in terms of sleep duration, and the sleep duration of a sample differs by more than an hour from the desired sleep duration set by the user, processor 115/135 or engine 310 may identify those two samples as being quantitatively dissimilar. Other factor quantities and similarity thresholds that may identify quantitatively similar samples may include wake durations differing by less than two hours, sleep interruptions differing by less than 15 minutes, wake times differing by less than an hour, waking up inside/outside a circadian trough or any combination thereof. Furthermore, if a user indicates that his sleep data recorded in a sample is abnormal, processor 115/135 or engine 310 may ignore that data as dissimilar.

However, if processor 115/135 or engine 310 is configured to perform similarity processing based on intra-personal analyses, the similarity thresholds for comparing two samples may be altered. If the homeostatic factor is quantified as sleep duration, and vigilance scores are strongly correlated to the homeostatic factor, the threshold between quantitatively different sleep times may be proportionally reduced according to the beta weight of the homeostatic component. Other intra-personal analyses may be applied as described in the foregoing System Operation section.

Equipped with the identities of any samples determined as quantitatively similar, action 635 may include local processor 115, remote processor 135 or recommendation engine 315 selecting a treatment sample, or a block of treatment samples, associated with the most desirable test scores. If only one sample is to be selected, processor 115/135 or engine 315 may simply select the quantitatively similar sample that has the most desirable test score. In the case of reducing sleep inertia severity, selecting a single sample may include selecting the sample with the highest vigilance test score among any quantitatively similar samples, since the highest score would indicate when sleep stage is lightest.

Alternatively, where a block of samples is to be selected, processors 115/135 or engine 315 may divide the sampling window into blocks based on different wake-up times. Each block may then have at least one sample. If more than one sample exists for each block, those samples may be combined to produce an aggregate score. The aggregate scores may then be analyzed to identify the block with the most desired aggregate score, such as a local max, indicating the highest aggregate vigilance scores within the sampling window of wake-up times.

However, if processor 115/135 or engine 315 detects a priority behavior condition, action 635 may override any recommendations by selecting the sample within the sampling window that is most desirable for treating the priority condition. For example, if processor 115/135 or engine 315 determines that a user is sleep deprived, the latest possible wake-up time within the sampling window may be selected as the treatment sample despite any recommendations to the contrary. As another example, if a recommended treatment sample would cause the wake-up time to fall within the trough of the user's circadian rhythm, the sample furthest from the peak of the circadian trough may be selected as the treatment sample.

Action 640 may include local processor 115, remote processor 135 or feedback engine 320 determining behavioral feedback based on the samples recommended as treatment samples in action 635. Where the treatment sample includes a single sample, behavioral feedback may be determined according to the proxy data of the single sample. For example, if the treatment sample indicates a wake-up time of 8:00 AM, the feedback will be an alarm of 8:00 AM. However, where a block of samples is recommended by action 635 for treating sleep inertia severity, action 640 will determine multiple instances of feedback to be used in the next iteration of action 620 based on the multiple wake-up times within the block of samples. For example, action 640 may determine wake-up times within a 15-minute sampling window as opposed to a 30-minute sampling that was used in a previous iteration of process 510. By reducing the sampling window used in each next iteration of action 620, each iteration of process 510 may produce a set of alarms with wake-up times that converge towards a wake-up time that best reduces sleep inertia severity.

In some cases, the local extreme within a sampling window may actually be less extreme than a local extreme observed in a previous sampling window. If that occurs, action 640 may include processor 115/135 or feedback engine 320 expanding the sampling window used by the processor 115/135 or probe and sample engine 305 in the next iteration of process 510. Accordingly, the expanded sampling window may include the currently recommend treatment samples and the block with the previously observed extreme. Alternatively, action

640 may include setting the sampling window for the next iteration of process 510 to include the block having the previously observed extreme.

FIG. 7A to FIG. 7G depict an embodiment of user interfaces for collecting behavioral data 105. These interfaces may be displayed by output means 150 or probe and sample engine 305. Examples of habits surveys may include questions 705, 710, 715, 720, 725 and 730 as displayed by the user interfaces depicted in FIG. 7A to FIG. 7C. A user's responses to questions 705, 710, 715, 720 and 725 may determine broad trends in an individual's behavior, such that processor 115/135 or engine 305 may quantify a user's circadian rhythm as a factor quantity in act 410.

FIG. 7D and FIG. 7E depict an embodiment of user interfaces displaying sleep surveys according to a modified Stanford Sleepiness Scale (SSS)™. The user's responses to questions 735, 740, 745 and 750 may enable processor 115/135 or engine 305 to quantify a user's homeostasis as a factor quantity in act 410.

FIG. 7F depicts an embodiment of a user interface for establishing alarm settings 755 and a user interface for specifying the quality of sleep 760. Component 755 may be a button enabling a user to accept all data set within interface 755. Button 755b may enable a user to set the number of minutes in which a user will experience sleep onset (e.g., 5, 15 or 30 minutes). A user may set a preferred time to wake by virtually spinning the wheels of component 755c. Interface 755 may display a projected wake-up time 755d according to produced behavioral feedback. Component 755e may be a button enabling a user to inform system 100 that the user has taken a nap earlier in the day. Component 760a may enable a user to indicate if he wakes during the night, and for the how long. Interface 760 may accordingly display a new projected wake-up time 760b. System 100 may display interface 760 after a user presses button 755a. The data input by a user through interfaces 755 and 760 may enable processor 115/135 or engine 305 to quantify a user's homeostasis as a factor quantity in act 410.

FIG. 7G depicts an embodiment of two interfaces. The first is interface 765 that represents a vigilance task that may be administered at different times of the day. The purpose of this vigilance task is to determine sleep inertia. Specifically, interface 765 displays icon 765a. A user may touch the icon. After being touched by a user, icon 765a may move to a new position, such as 765b and 765c. A user may then follows icon 765a to the new positions with his finger, or another pointing device. The faster the user follows icon 765a, the faster icon 765a may move about interface 765. Processor 115/135 or engine 305 may determine a user's vigilance score by calculating the distance a user's finger travels in a predetermined time period—the greater the distance traveled, the greater the vigilance score.

An embodiment of the second interface depicted by FIG. 7G is a sleep quality interface 770. This interface may determine whether the behavioral data 105 captured in act 405 is statistically valid. If a user indicates that his sleep was abnormal, the data associated with that sleep may be ignored by processor 115/135 or engine 305.

It should be noted that systems 100 and 300 illustrate embodiments of systems for treating cyclical behaviors according to process 510. The illustrated components may be eliminated or configured in multiple embodiments. For example, where local processor 115 acts alone, all foregoing actions of process 530 may occur within processor 115 without the intervention of components 120, 125, 130 or 135. On the other hand, where remote processor 135 acts alone, all foregoing processing step may occur within processor 135 with processor 115 merely serving to pass data to/from remote processor 135, input means 110 and output means 150. Communication means 120 may pass behavioral data to network 125, network 125 may pass the behavioral data to communication means 130 and means 130 may pass the behavioral data to remote processor 135. The behavioral feedback 155 may accordingly passed back from remote processor 135 to output means 150 through communication means 130, network 125, communication means 120 and/or local processor 115. The engines of system 300 may be embodied together in a single device or in a system of interconnected devices.

The foregoing description of process 510 focused on an embodiment where the cyclical behavior of interest was sleep inertia severity. In general, process 510 may be used for any other sleep behavior affected by cyclical factors. For example, other sleep behaviors susceptible to treatment by systems 100 and 300 may include reducing sleep onset, improving dream recollection, length of sleep, when to sleep, when and how long to nap, and/or any combination thereof. In addition to determining descriptions of circadian and homeostatic components, systems 100 and 300 may also determine factor data to describe other factors, including sleep stage when awakened, whether a person is a morning-person or an evening-person, demographic factors, like gender and profession, and daily factors, like stress, anxiety, food intake, exercise, lunar cycle, weather, mood, drug use, physical ailment, work schedule, GPS location and/or sleep environment. Finally, systems 100 and 300 may estimate the effects any of the foregoing factors have on a sleep behavior.

The description in this section sets forth an embodiment for treating cyclical sleep behaviors. Other sections of this description set forth examples concerning other forms of cyclical behavior. Of course, other forms of behavior are susceptible to treatment by the data processing system 100 and the behavior treating system 300. For instance, systems 100 or 300 may be configured to treat susceptibility to drug relapses, psychotic disorders, physiological disorders, medication dosages, ability to learn, personality traits, creativity, analytical thinking and/or any combination thereof.

Treating Depression

Figure 8A:
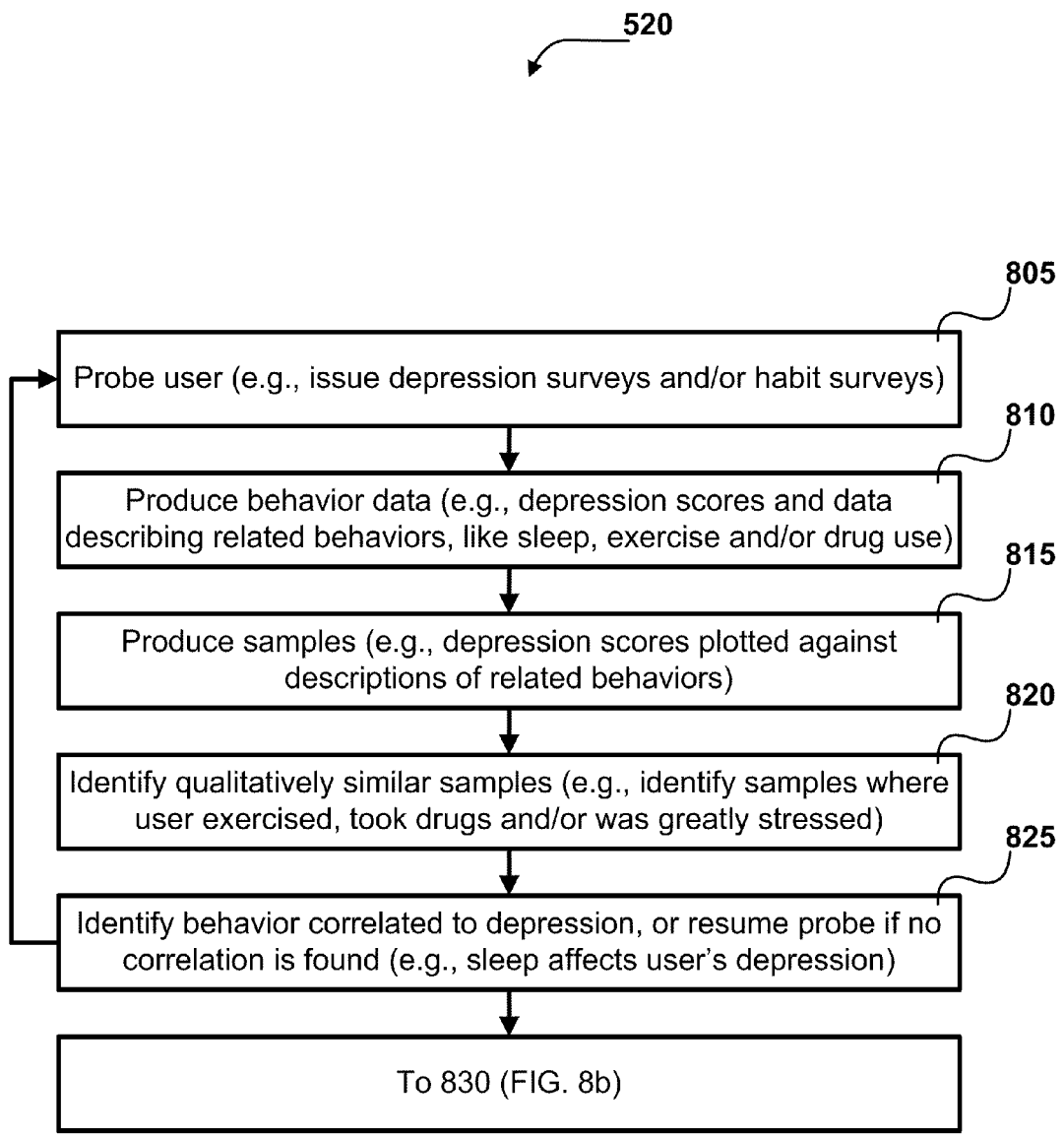
FIG. 8A and FIG. 8B depict an embodiment of actions for treating depression according to FIG. 5.
Figure 8B:
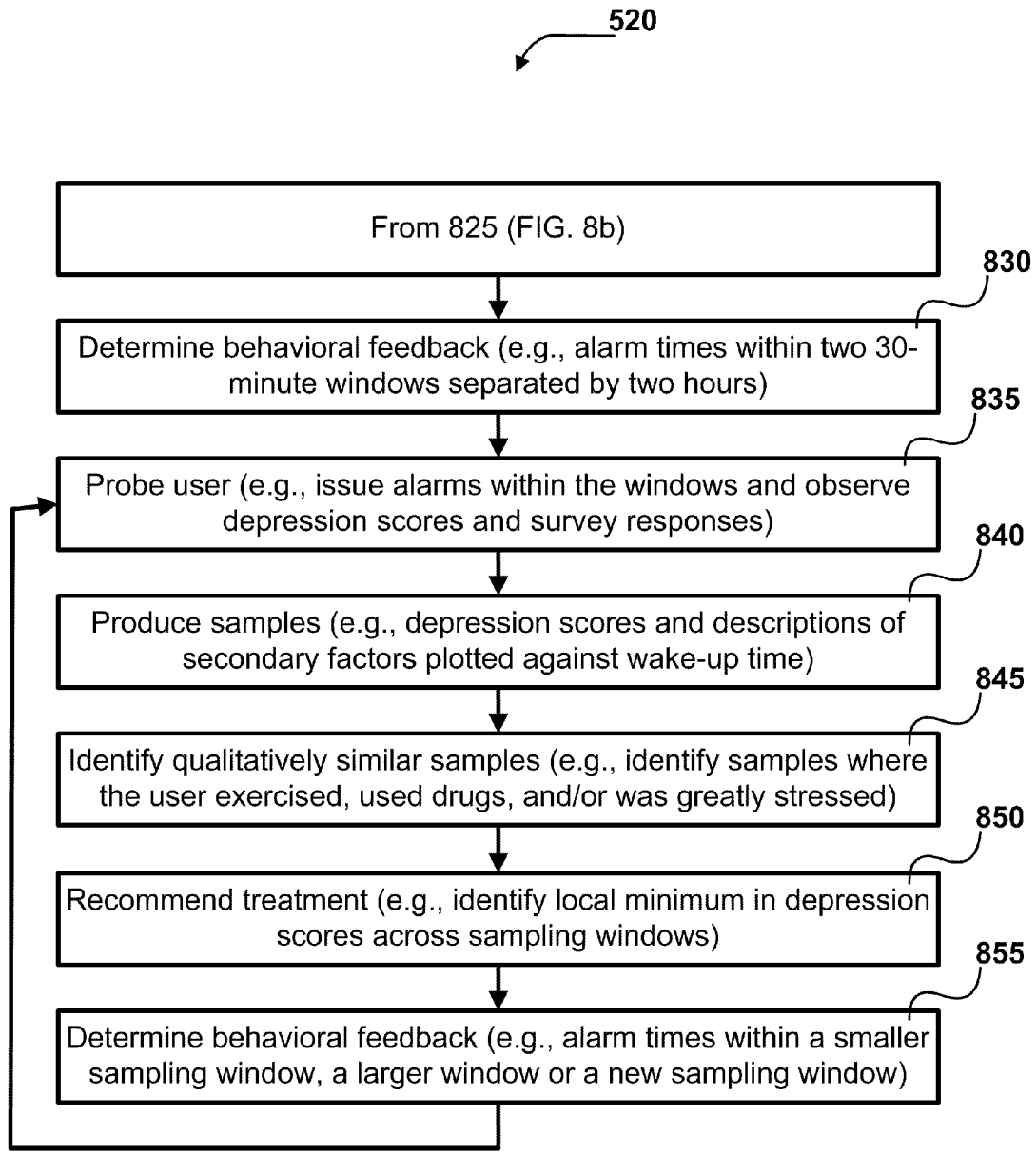

Returning to FIG. 5, another portion of cyclical behavior treatment process 500 may include a depression evaluation and treatment process 520 executed by local processor 115, remote processor 135 or system 300 according to program 275. FIG. 8A and FIG. 8B depict an embodiment of process 520. Process 520 is similar to processes 300 and 510, but differs because process 520 may include a sampling procedure to determine a behavior that co-varies with depression. Upon identifying a behavior that co-varies with depression, process 520 may estimate how at least one factor related to the co-varying behavior affects depression severity.

Actions 805 and 810 may include using input means 110, output means 150 or engine 305. The actions may be similar to actions 320 and 325, but may further include probing a user by issuing daily surveys and ascertaining a depression score indicating the severity of a user's depression. Moreover, actions 805 and 810 may include issuing daily habit surveys and ascertaining general trends in other behaviors suspected to contribute to depression severity, including sleep amount, sleep quality, exercise type, exercise duration, exercise intensity, drug use and/or medication use.

Action 815 may include using local processor 115, remote processor 135 or engine 305. Action 815 may operate analogously to action 325. Further, action 815 may produce samples of behavior data, which is analogous to factor data, but describes behaviors instead of factors. Each sample of behavior data may include descriptions of secondary behaviors, score data reflecting depression severity, proxy data or any combination thereof. However, the proxy data here need not actually be a proxy for a behavior, but may be a more direct description of the behavior. Ultimately, proxy data may be any data that has at least two values, such that an effect of the behavior on depression severity scores may be assessed.

Action 820 performs a similarity analysis that is analogous to action 330 to determine whether any samples of behavior data are quantitatively similar. In an embodiment, action 820 includes using local processor 115, remote processor 135 or similarity engine 310. For instance, if a user has indicated that he desires to exercise three times a week and a sample indicates that he exercised less than three times in a week, the sample may be ruled quantitatively dissimilar. If a user is taking depression medication and a sample indicates he failed to take his medicine, that failure may cause the sample to fail the similarity analysis.

Using any quantitatively similar samples, action 825 may include using local processor 115, remote processor 135 or recommendation engine 315 to perform a correlation analysis between the proxy data for a behavior suspected to co-vary with depression severity and scores indicating depression severity. If the R-value of the correlation analysis indicates a correlation of at least greater than 0.20, process 520 may continue on to action 830 to estimate the effects at least one factor the co-varying behavior has on depression intensity. Otherwise, the processors of system 100 or the engines of system 300 repeat actions 805 to 825 to test another behavior suspected to co-vary with depression intensity.

Actions 830 to 855 are analogous in operation to actions 315 to 340 and actions 615 to 640, but operate on different sets of data to achieve treatment of depression severity. According to an embodiment depicted in FIG. 8B, the processors of system 100 or the engines of system 300 have determined that sleep is co-varying with a user's depression intensity. In that case, process 520 may include considering length of sleep (e.g., the homeostatic factor) as a sleep related factor that may be affecting depression. Accordingly, action 830 may include using local processor 115, remote processor 135 or feedback engine 320 to determine behavioral feedback as multiple alarm times across at least two 30-minutes sample windows separated by two hours. Action 835 may then use processor 115/135 or engine 305 to randomly issue the alarms within the first window over a period of days and then issue the alarm within the second window over another period of days. The probing in action 835 may further include gathering depression scores from depression tests issued at the end of the day. Of course, the depression tests may be issued at other times throughout the day as a user desires. In any case, by using processor 115/135 or engine 305, action 840 produces samples of factor data including descriptions of secondary factors, depression severity scores and proxy data indicating wake-up times.

Action 845 may include using processor 115/135 or similarity engine 310 to perform a similarity analysis on the samples produced in action 840. In the depression severity context when sleep is identified as a co-varying behavior, the descriptions of secondary factors compared in the similarity analysis may include time of day when awoke (e.g., circadian factor), exercise amount, exercise intensity, drug use and/or medication use. As in action 820, if a user indicates that he desires to exercise three times a week, but a sample indicates that the user failed to meet that minimum, or exercised much more, that sample may be ruled quantitatively dissimilar.

Action 850 may include using local processor 115, remote processor 135 or recommendation engine 315 to recommend treatment based on any samples determined to be quantitatively similar. For instance, samples with depression severity scores, plotted against wake-up time in a sampling window, representing a local minimum in a window may be identified as treatment samples. Of course, a window may be divided into blocks of samples, and the block with the lowest aggregate depression score may be identified as a block of treatment samples. In addition, where the feedback includes at least two sample windows, a local minimum from each window may be determined, and then the treatment sample may be selected as the sample, or block of samples, associated with the lowest depression severity score across the windows.

Action 855 may include using local processor 115, remote processor 135 or feedback engine 320 to determine updated behavioral feedback based on the proxy data of the treatment sample identified in action 850. If a block of treatment samples is identified, however, action 855 may determine multiple instances of alarms at each wake-up time within the block of treatment samples. In this way, the sampling window in the next iteration of process 520 decreases in size. Thus, process 520 may converge over time on an optimal treatment for depression severity. Of course, action 855 may include expanding the window if the currently defined window produced worse behavioral results then a previously defined window. Moreover, action 855 may include defining an entirely new window with previously untested proxy values.

FIG. 9A depicts an embodiment of a depression severity survey 905 and an exercise survey 910. These surveys may be displayed using output means 150 or probe and sample engine 305. Survey 905 may enable system 100 to assess a user's depression level based on questions that may include questions 905a, 905 and 905c. Survey 910 may enable system 100 to assess a user's daily exercise based on answers to questions 910a and 910b.

FIG. 9B depicts an embodiment of a further exercise survey 915, whose questions 915a and 915b may produce data on a user's daily exercise. This survey may be displayed using output means 150 or probe and sample engine 305. In addition, FIG. 9B depicts a secondary factor/behavior survey 920 that may include a stress question 920a, a medication question 920b and a drug question 920c. The answers to these questions may enable system 100 to assess a user's stress level, medication use and drug use.

It should be noted that systems 100 and 300 illustrate embodiments of systems for treating cyclical behaviors according to process 520. The illustrated components may be eliminated or configured in multiple embodiments. For example, where local processor 115 acts alone, all foregoing actions of process 530 may occur within processor 115 without the intervention of components 120, 125, 130 or 135. On the other hand, where remote processor 135 acts alone, all foregoing processing step may occur within processor 135 with processor 115 merely serving to pass data to/from remote processor 135, input means 110 and output means 150. Communication means 120 may pass behavioral data to network 125, network 125 may pass the behavioral data to communication means 130 and means 130 may pass the behavioral data to remote processor 135. The behavioral feedback 155 may accordingly passed back from remote processor 135 to output means 150 through communication means 130, network 125, communication means 120 and/or local processor 115. The engines of system 300 may be embodied together in a single device or in a system of interconnected devices.

The foregoing description of process 520 suggested some types of behaviors that co-vary with depression and factors of those behaviors that may be analyzed for their effect on depression. In general, process 510 may be used for treating depression severity based on any behavior that co-varies with depression severity and any cyclical factor of a behavior that effects depression severity.

The description in this section sets forth an embodiment for treating cyclical depression behaviors. Other sections of this description set forth examples concerning other forms of cyclical behavior. Of course, other forms of behavior are susceptible to treatment by the data processing system 100 and the behavior treating system 300. For instance, systems 100 or 300 may be configured to treat susceptibility to drug relapses, psychotic disorders, physiological disorders, medication dosages, ability to learn, personality traits, creativity, analytical thinking and/or any combination thereof.

Treating Behaviors Affected by Exercise

Figure 10:
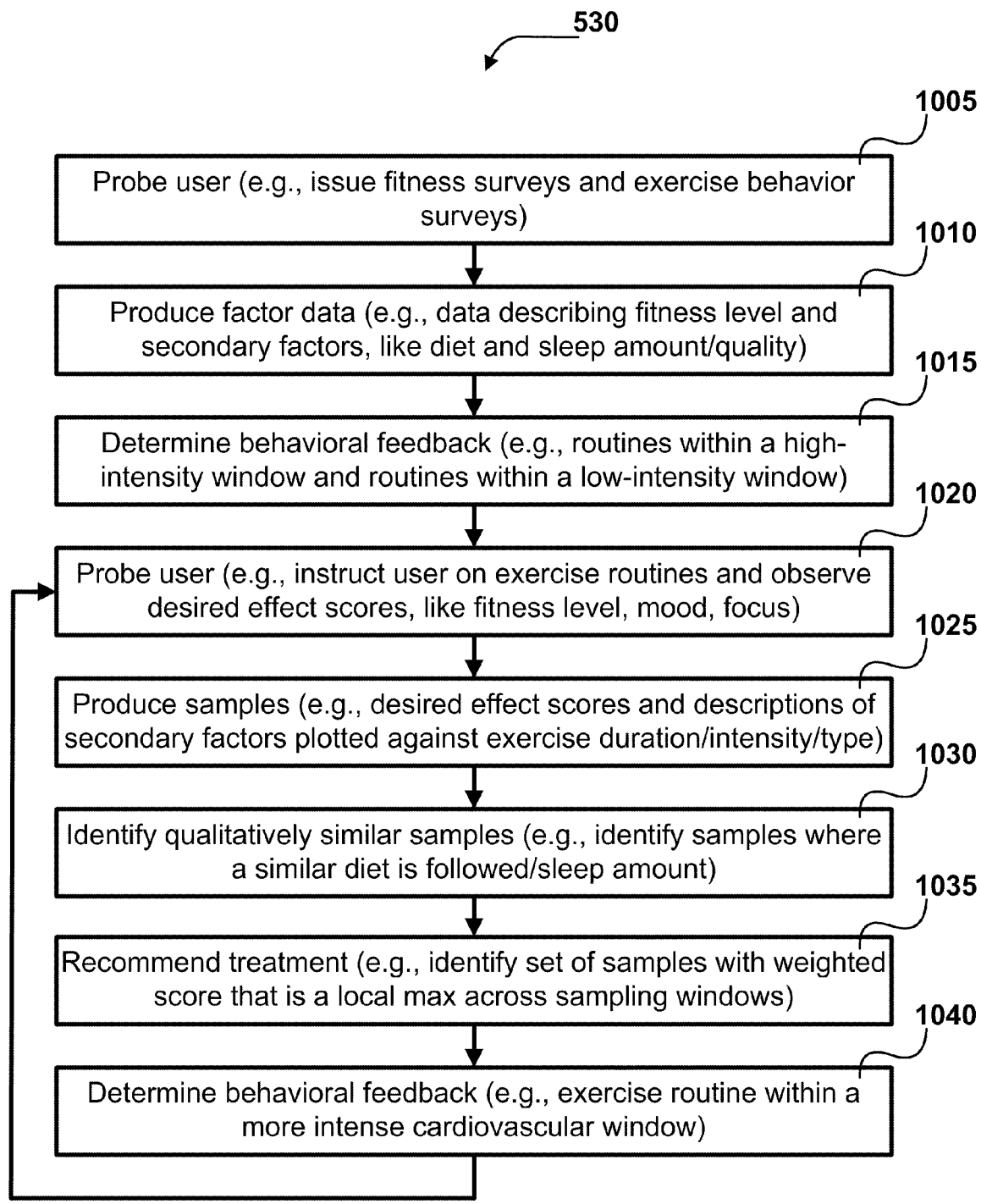
FIG. 10 depicts an embodiment of actions for treating behaviors affected by exercise according to FIG. 5.

Returning to FIG. 5, another portion of cyclical behavior treatment process 500 may include an exercise evaluation and treatment process 530 executed by local processor 115, remote processor 135 or system 300 according to program 280. FIG. 10 depicts an embodiment of process 530 for treating behaviors that may be affected by exercise ("exercise behaviors"). Process 530 is generally similar to processes 300 and 510. Indeed, Actions 1005 to 1040 are analogous in operation to actions 305 to 340 and actions 605 to 640, but operate on data related to exercise.

Action 1005 may include using input means 105 and output means 150 or probe and sample engine 305 to probe a user with fitness surveys and exercise behavior surveys. Examples of fitness surveys may include those depicted in FIG. 11A and FIG. 11B, described below. These fitness surveys may provide general information concerning a user's fitness level so system 100 may calibrate the initial set of behavioral feedback that will be issued to improve a user's exercise behavior. The exercise behavior surveys, such as survey 1125 of FIG. 11C, described below, indicate the relative importance of various exercise behaviors whose optimal treatments may be in tension. The relative importance of various exercise behaviors may be used by system 100 to adjust feedback to maximize improvements across various exercise behaviors according to user desires.

Action 1010 produces descriptions of exercise-related factors based on the fitness surveys. For instance, action 1010 may include using local processor 115, remote processor 135 or probe and sample engine 305 to produce a description of how fit a user.

Action 1015 may use processor 115/135 or engine 320 to consequently produce feedback in light of these factor descriptions, as well as the relative importance of various exercise behaviors. Thus, if a user is not very fit, the feedback produced in action 1015 may include exercise instructions for low intensity or short duration exercise to avoid injury. Moreover, if the relative importance of cardiovascular strength is emphasized over muscular strength, the feedback may include exercise instructions to perform cardiovascular activities three times a week while lifting weights only twice a week. The recommendations produced in action 1015 may also include multiple instances of recommendations. Recommendations, for example, may suggest exercising three times for one week, and exercising two times a week for a second week.

Action 1020 uses input means 105 and output means 110 or probe and sample engine 305 to issue all instances of feedback produced in step 1015. Moreover, action 1020 may use local processor 115/135 or engine 305 to observe user responses to the feedback and obtain data associated with the responses. The user responses may include answers to exercise surveys, energy surveys, weight surveys, focus surveys, stress surveys and/or diet surveys. Interfaces for these surveys may include those depicted in FIG. 11C to FIG. 11F, described below. FIG. 12 depicts an embodiment of an optional mode for obtaining user responses. In that embodiment, user responses may further include exercise duration/intensity measurements obtained by local processor 115/135 or engine 305 using an accelerometer, such as a wrist-worn accelerometer 115b attached to a user's wrist, and which transmits accelerometer measurements to a local processor 115a, like local processor 115 or engine 305.

Action 1025 uses local processor 115, remote processor 135 or engine 305 to produce samples from the user responses. The exercise surveys may provide proxy data by indicating the types, intensity and duration of exercise. The exercise surveys, energy surveys, weight surveys, focus surveys, stress surveys or any combination thereof may provide score data for exercise behaviors, such as strength gain, energy gain, weight loss, focus gain, stress reduction or any combination thereof. Finally, diet surveys may provide comparison data by describing a user's diet.

Action 1030 may use local processor 115, remote processor 135 or similarity engine 310 to perform a similarity analysis on the samples produced in action 1025. In the exercise behavior context, the descriptions of secondary factors compared in the similarity analysis may include diet and/or amount of sleep. If a user indicates that he desires to sleep eight hours a day, but a sample indicates that he only slept six hours one day, that sample may be ruled quantitatively dissimilar.

Using local processor 115, remote processor 135 or recommendation engine 315, action 1035 may recommend treatment based on any samples determined to be quantitatively similar. For instance, samples with stress scores, plotted against exercise intensity in a sampling window, representing a local minimum in a window may be identified as treatment samples. As in the general, sleep and depression contexts, a window may be divided into blocks of samples, and the block with the lowest aggregate stress score may be identified as a block of treatment samples. In addition, where the feedback includes at least two sample windows, a local minimum from each window may be determined, and then the treatment sample may be selected as the sample, or block of samples, associated with the lowest depression severity score across the windows.

Where a user indicates the relative importance of multiple exercise behaviors, action 1035 may use processor 115/135 or engine 315 to recommend a treatment based on a weighted combination score. Essentially, action 1035 may weigh the score of each sample according to the relative importance of the exercise behavior to which the score pertains. If a user indicates that weight loss is very important, but focus gain is not very important, scores pertaining to weight loss may be weighted heavily and scores pertaining to focus gain may be weighted less heavily. The weighted scores may then be combined into the weighted combination score.

Action 1040 may use local processor 115, remote processor 135 or feedback engine 320 to determine updated behavioral feedback by producing recommendation alarms based on the proxy data of the treatment sample identified in action 1035. If a block of treatment samples is identified, however, action 1040 may determine multiple instances of recommendations at each recommended exercise intensity and/or duration level within the block of treatment samples. In this way, the sampling window in the next iteration of process 530 decreases in size. Thus, as in processes 300, 510 and 520, process 530 may converge over time on an optimal treatment for exercise behaviors.

Figure 11A:
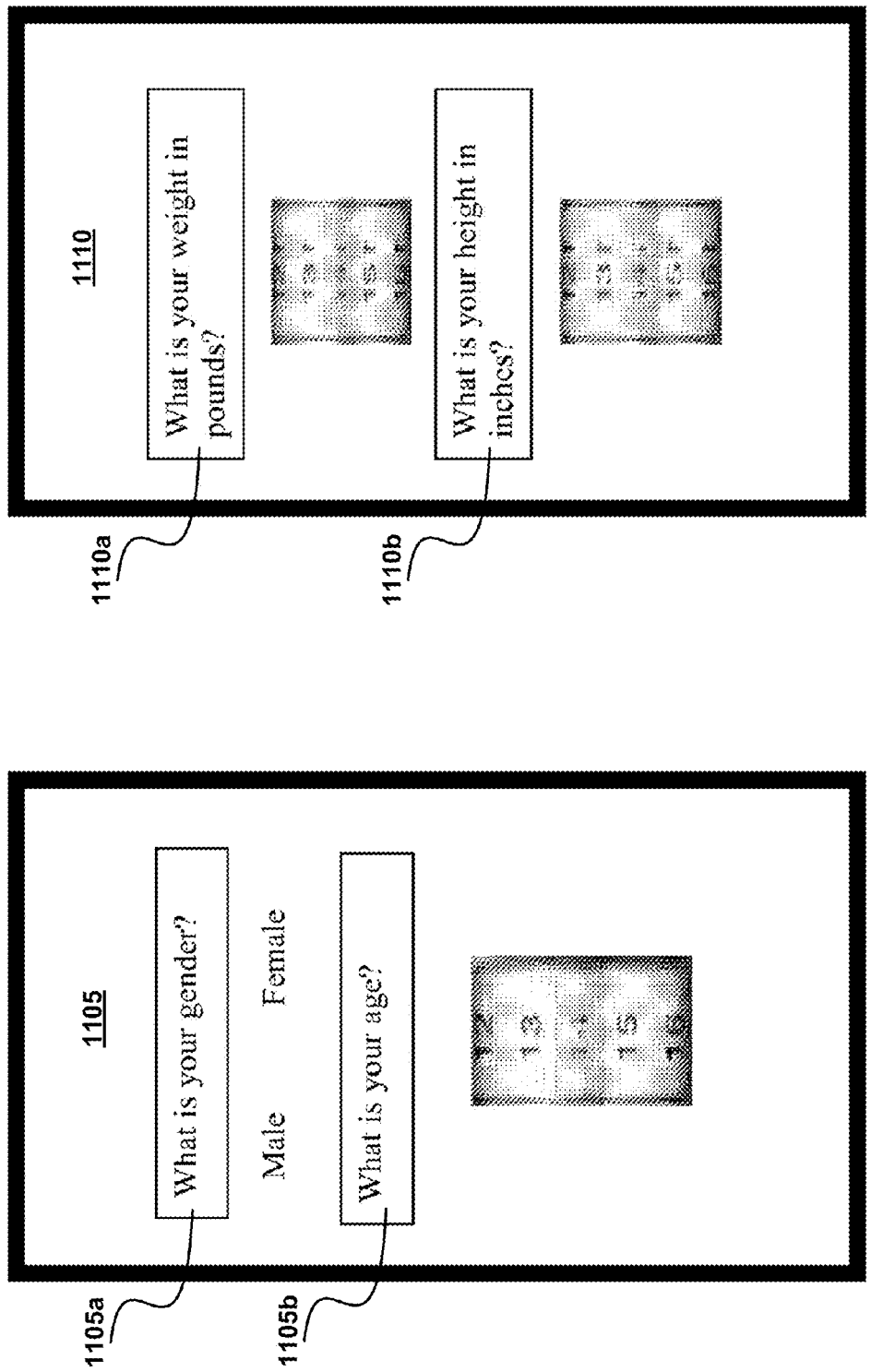
Figure 11B:
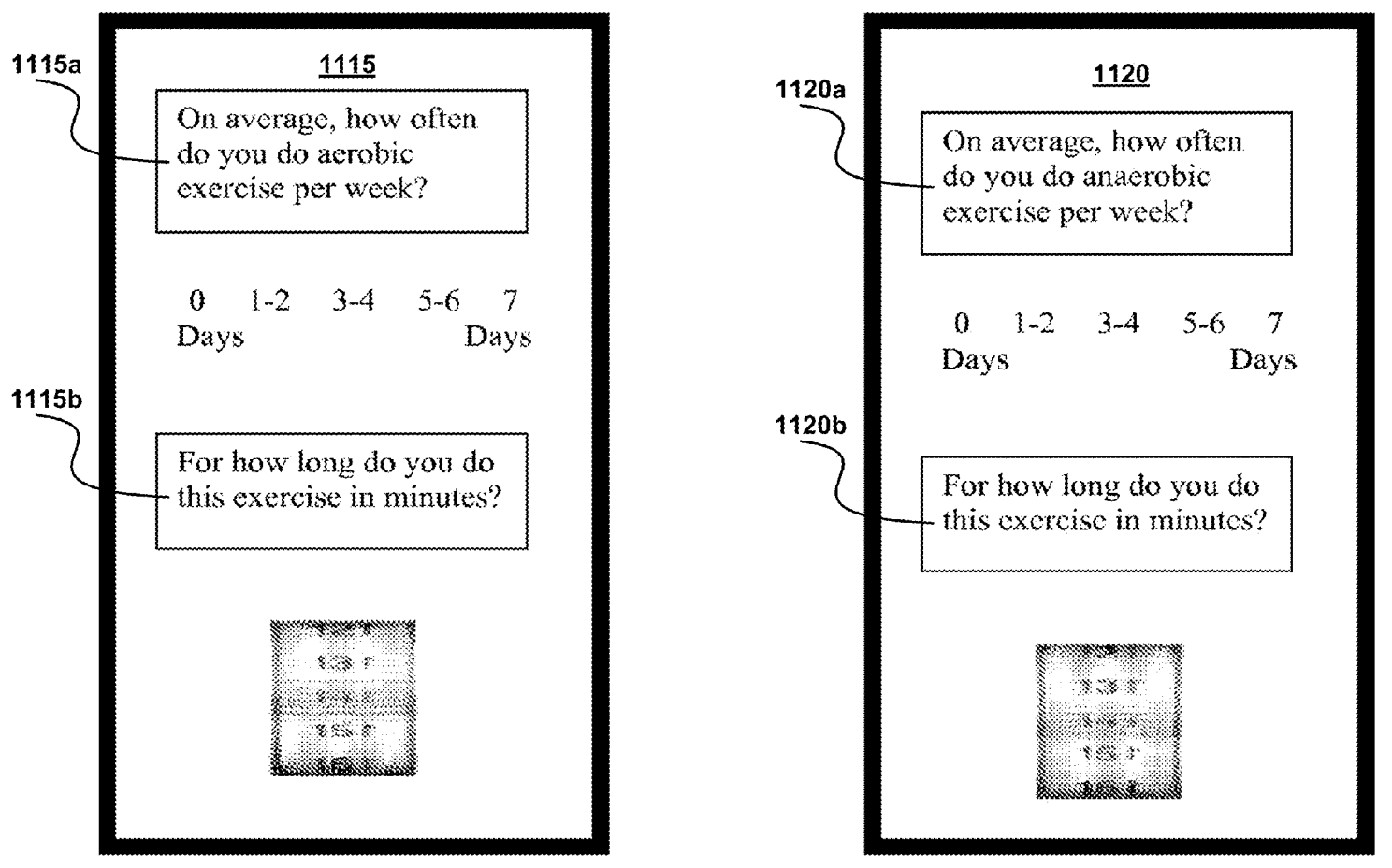
Figure 12:
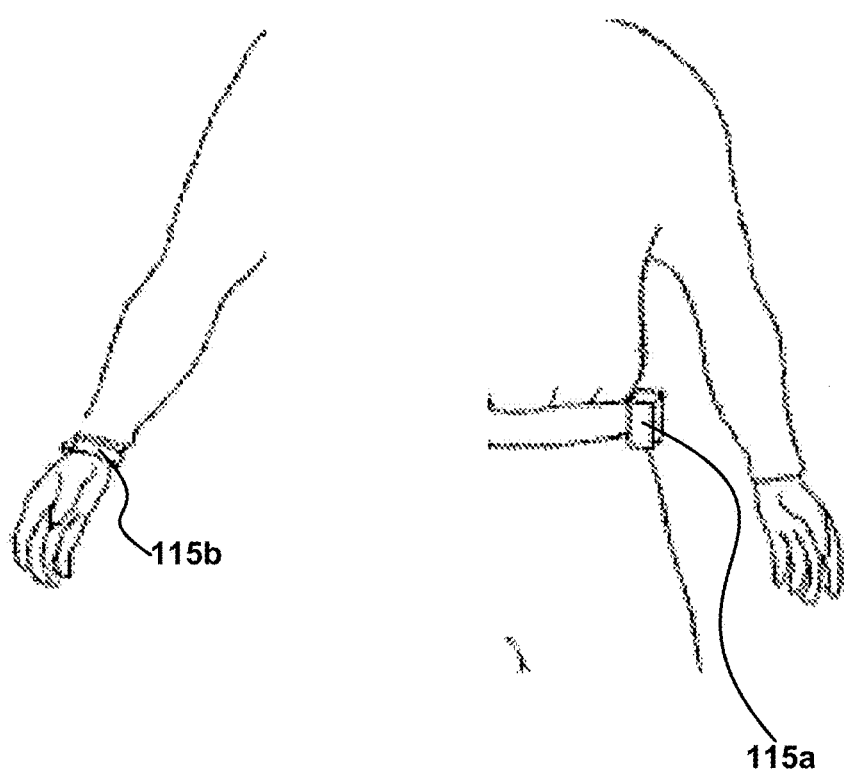
FIG. 12 depicts an embodiment of an arrangement for implementing the local processor of the data processing system of FIG. 1.

FIGS. 11A and 11B depicts an embodiment of fitness surveys 1115, 1120, 1125 and 1130. Questions 1115a, 1115b, 1120a, 1120b, 1125a, 1130a and 1130b may provide general information on a user's fitness level.

Figure 11C:
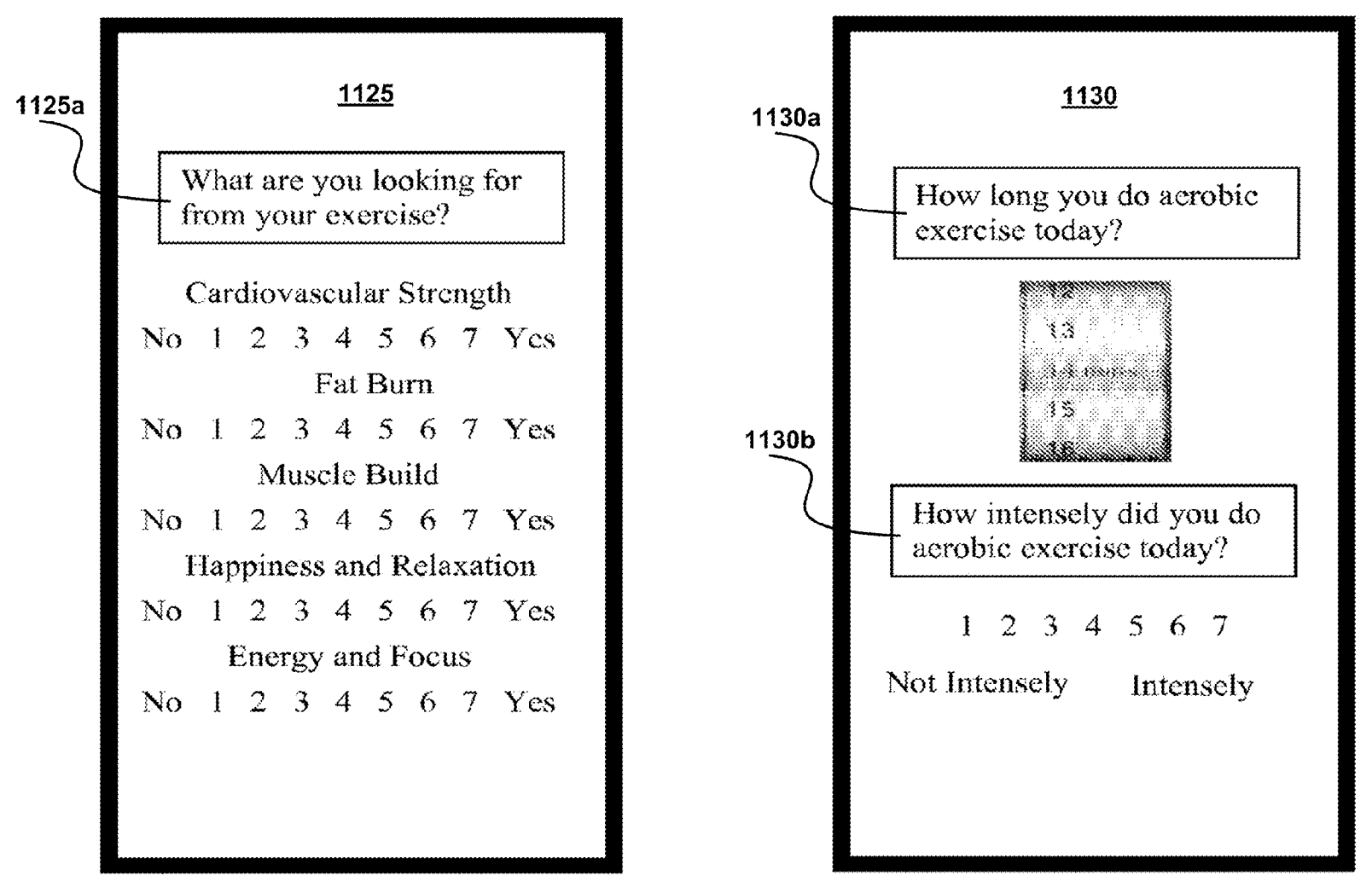

FIG. 11C depicts an embodiment of an exercise behavior survey 1125. A user may answer question 1125a of survey 1125 to indicate the relative importance of various exercise behaviors.

Figure 11D:
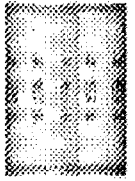
Figure 11D:
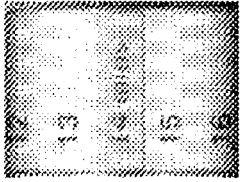

FIG. 11C also depicts an embodiment of an exercise survey 1130. FIG. 11D depicts an embodiment of further exercise surveys 1135 and 1140. Surveys 1130 to 1140 may include questions 1130a, 1130b, 1135a, 1135b, 1140a, 1140b and 1140c that may enable system 100 to ascertain the level, intensity and type of exercise a user performs on a daily basis.

Figure 11E:
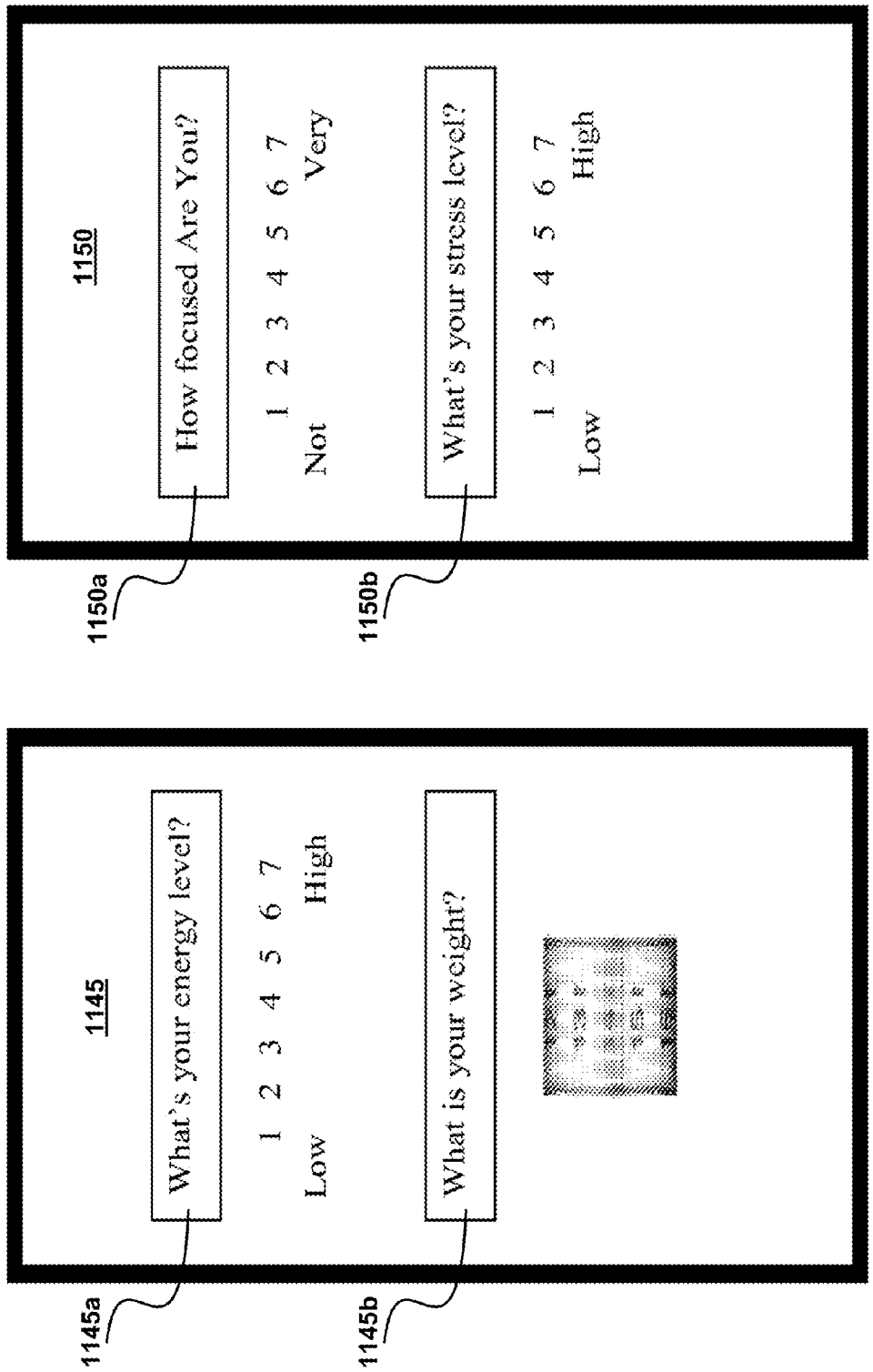

FIG. 11E depicts an embodiment of surveys 1145 and 1150, which may include an energy question 1145a, a weight question 1145b, a focus question 1150a and a stress level question 1150b for ascertaining a user's energy level, weight loss, focus level and stress level. FIG. 11f depicts an embodiment of a diet survey 1155 that may include a set of diet question 1155a so system 100 may ascertain a user's diet.

It should be noted that systems 100 and 300 illustrate embodiments of systems for treating cyclical behaviors according to process 530. The illustrated components may be eliminated or configured in multiple embodiments. For example, where local processor 115 acts alone, all foregoing actions of process 530 may occur within processor 115 without the intervention of components 120, 125, 130 or 135. On the other hand, where remote processor 135 acts alone, all foregoing processing step may occur within processor 135 with processor 115 merely serving to pass data to/from remote processor 135, input means 110 and output means 150. Communication means 120 may pass behavioral data to network 125, network 125 may pass the behavioral data to communication means 130 and means 130 may pass the behavioral data to remote processor 135. The behavioral feedback 155 may accordingly passed back from remote processor 135 to output means 150 through communication means 130, network 125, communication means 120 and/or local processor 115. The engines of system 300 may be embodied together in a single device or in a system of interconnected devices.

The foregoing description of process 530 suggested some types of exercise behaviors and factors to consider in treating those behaviors. In general, process 530 may be used for treating any type of exercise behavior based on any cyclical factor that affects an exercise behavior.

The description in this section sets forth an embodiment for treating cyclical behaviors affected by exercise. Other sections of this description set forth examples concerning other forms of cyclical behavior. Of course, other forms of behavior are susceptible to treatment by the data processing system 100 and the behavior treating system 300. For instance, systems 100 or 300 may be configured to treat susceptibility to drug relapses, psychotic disorders, physiological disorders, medication dosages, ability to learn, personality traits, creativity, analytical thinking and/or any combination thereof.

Summary

An embodiment may be instantiated as a non-transitory computer readable medium containing instructions that, when executed by or more processors, cause the one or more processors to perform an iterative process for treating cyclical behavior(s) based on behavioral data, the behavioral data describing physiological factors, the physiological factors correlating with the cyclical behavior(s). The process may include: collecting behavioral data from a user and extracting diverse factor data points that describe physiological factor(s) from the behavioral data. The factor data points may include: score data that describes how the physiological factors affect the cyclical behavior(s); comparison data that describes how quantitatively similar factor data points affect the physiological factor(s); and proxy data that describes a variable that correlates the relationship between the quantitatively similar factor data points.

From the quantitatively similar factor data points, treatment data based on an estimate of how the quantitatively similar factor data points affect the cyclical behavior(s) may be recommended. Behavioral feedback may be formulated and issued from the treatment data to produce new behavioral data. Embodiments may further include determining if one of the factor data points is quantitatively similar to another of the factor data points.

The determining if one of the factor data points is quantitatively similar to another of the factor data points may include: calculating, on a factor-wise basis, at least one set of distances between the comparison data of one of the factor data points and the comparison data of the another of the factor data points; and deciding that the one of the factor data points is quantitatively similar to another of the factor data points if the distances are within at least one threshold. At least one threshold may have a value that varies proportionately with the degree of dependence between score data and the comparison data.

Recommending treatment data may include: estimating how factor data point(s) affect cyclical behavior(s) by identifying, from among quantitatively similar factor data points, the factor data point(s)s whose score data has a desirable value; and recommending the treatment data based on the proxy data of the identified at least one of the factor data point.

Identifying treatment data may include: dividing sampling window(s) into at least one block; arranging any quantitatively similar factor data points into the blocks based on the proxy data of the quantitatively similar factor data points, such that at least one block contains at least one of the quantitatively similar factor data points; combining score data of at least one of the quantitatively similar factor data points in each of the blocks that contains factor data points to produce a combined score for each block; identifying the block that contains the desirable combined score as at least one a local extreme; and identifying as the treatment data at least one of the factor data points within the block identified as the at least one local extreme.

Cyclical behavior(s) may actually be at least two cyclical behaviors; and the score data of at least one of the quantitatively similar factor data points in each block may include a weighted combination of score data produced by combining at least one score associated with each of the at least two behaviors and weighted according to user preference data indicating the relative importance of the at least two cyclical behaviors.

The determining behavioral feedback may include determining the behavioral feedback based on the treatment data, such that, after several iterations of implementing behavioral feedback, score data associated with at least one response converges towards the score data of at least one of the factor data points identified in the treatment data.

The estimating treatment data may include: when the factor data indicates that a priority behavior condition exists, identifying at least one factor data point, from among the at least one quantitatively similar factor data points, whose proxy data indicates that the at least one factor data point would best improve the priority behavior condition; and estimating the treatment data based on the proxy data of the at least one factor data points.

The behavioral data may include at least one of the following: at least one survey response; at least one invasive physiological measure; at least one non-invasive physiological measure; at least one vigilance score concerning a user's performance of at least one vigilance task; at least one cognition score concerning a user's performance of at least one cognitive task; or any combination thereof. In some embodiments, the behavioral data may include at least one of the following: information relating to bedtime; wake time; at least one sleep quality survey; at least one sleep efficiency survey; at least one sleepiness survey; severity of depression; at least one habit survey; at least one medication use survey; invasively collected sample; non-invasively collected sample; a user's fitness level; a user's diet habits; a user's exercise habits; or any combination thereof.

The cyclical behavior(s) may include at least one of the following: sleep inertia; the homeostatic sleep need; the circadian sleep need; dream recall; reduction in sleep onset; best time and duration to nap; the best time to exercise; the best type of exercise; a healthier diet; increased productivity; improved mood; the best time to take a medication; the best dosage of medication; or any combination thereof. The cyclical behavior(s) may include a behavior that co-varies with depression severity. Embodiments may further include identifying, from the behavioral data, at least one cyclical behavior that co-varies with depression severity. The cyclical behavior(s) may include a behavior that co-varies with a fitness behavior. Embodiments may further include identifying at least one user-selected fitness behavior. In some embodiments, cyclical behavior(s) may include a behavior that co-varies with sleep interia.

The behavioral feedback may include at least one of the following: an alarm set at a wake-time; at least one indication of when to go to sleep; suggestion of amount of sleep; when to exercise; how much to exercise; sleep instructions; workout instructions; medication instructions; diet instructions; a vigilance task; or any combination thereof.

The physiological factor(s) may include at least one of the following: a homeostatic component; a circadian component; a sleep stage upon waking component; choronobiology; neurochemistry; physical cycles (i.e. periods, food needs, menopause, etc.); or any combination thereof.

In embodiments, each iteration may be performed within a sampling window; and the size of the sampling window may be modified based upon changes in behavioral data.

Conclusion

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e hardware with a biological element) or a combination thereof, all of which are behaviorally equivalent. For example, modules may be implemented as a software routine written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail may be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) of treating sleep behaviors, depression and behaviors affected by exercise. However, one skilled in the art will recognize that embodiments of the invention could include treating any behavior sensitive to cyclical factors, such as drug relapses, psychotic disorders, physiological disorders, medication dosages, ability to learn, personality traits, creativity, analytical thinking and/or any combination thereof.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A non-transitory computer readable medium containing instructions that, when executed by one or more processors, cause the one or more processors to perform an iterative process for treating at least two cyclical behaviors based on behavioral data, the behavioral data describing physiological factors, the physiological factors correlating with the at least two cyclical behavior, the process comprising:

a) collecting the behavioral data from a user;
   b) extracting at least two diverse factor data points that describes at least one physiological factor from the behavioral data to identify quantitatively similar factor data points by determining if one of the at least two diverse factor data points is quantitatively similar to another of the at least two diverse factor data points, the at least two diverse factor data points including:
  i) score data of at least one of the quantitatively similar factor data points that describes how the at least one physiological factor affect the at least one of the at least two cyclical behavior;
  ii) comparison data that describes how at least two of the quantitatively similar factor data points affect the at least one physiological factor; and
  iii) proxy data that describes a variable that correlates the relationship between the at least two quantitatively similar factor data points;
c) identifying treatment data including:
  i) dividing at least one sampling window into at least one block;
  ii) arranging any of the quantitatively similar factor data points into at least one of the at least one block based on the proxy data of the quantitatively similar factor data points, such that the at least one block contains at least one of the quantitatively similar factor data points;
  iii) combining the score data of at least one of the quantitatively similar factor data points in each of the at least one block that contains the quantitatively similar factor data points to produce a combined score for each of the at least one block, wherein the score data of the at least one quantitatively similar factor data points in each of the least one block includes a weighted combination produced by combining at least one score associated with each of the at least two cyclical behaviors and weighted according to user preference data indicating the relative importance of the at least two cyclical behaviors;
  iv) identifying at least one block that contains a desirable combined score as at least one local extreme; and
  v) identifying as the treatment data at least one of the quantitatively similar factor data points within the at least one block that contains the desirable combined score as the at least one local extreme.
d) recommending, from the at least two quantitatively similar factor data points, the treatment data based on:
  i) an estimate of how at least one of the quantitatively similar factor data points affects at least one of the at least two cyclical behavior by identifying, from among the quantitatively similar factor data points, at least one of the quantitatively similar factor data points whose score data has a desirable value; and
  ii) on the proxy data of the at least two quantitatively similar factor data points,
e) formulating, from the treatment data, behavioral feedback configured to produce new behavioral data; and
f) issuing the behavioral feedback.

2. The medium of claim 1, wherein the determining if one of the at least two diverse factor data points is quantitatively similar to another of the at least two diverse factor data points includes:
  a) calculating, on a factor-wise basis, at least one set of distances between the comparison data of one of the at least two diverse factor data points and the comparison data of the another of the at least two diverse factor data points; and
  b) deciding that the at least two diverse factor data points are quantitatively similar if the distances are within at least one threshold.

3. The medium of claim 2, wherein the at least one threshold has a value that varies proportionately with the degree of dependence between the score data and the comparison data.

4. The medium of claim 1, wherein formulating the behavioral feedback includes determining the behavioral feedback based on the treatment data, such that, after several iterations of implementing behavioral feedback, score data associated with at least one response converges towards the score data of at least one of the at least two diverse factor data points identified in the treatment data.

5. The medium of claim 1, comprising estimating treatment data including:
  a) when the at least two diverse factor data points indicate that a priority behavior condition exists, identifying at least one of the at least two diverse factor data point, from among at least one of the quantitatively similar factor data points, whose proxy data indicates that the at least one of the at least two diverse factor data point would best improve the priority behavior condition; and
  b) estimating the treatment data based on the proxy data of the at least one factor data point.

6. The medium of claim 1, wherein the behavioral data includes at least one of the following:
  a) at least one survey response;
  b) at least one invasive physiological measure;
  c) at least one non-invasive physiological measure;
  d) at least one vigilance score concerning a user's performance of at least one vigilance task;
  e) at least one cognition score concerning a user's performance of at least one cognitive task; or
  f) any combination thereof.

7. The medium of claim 1, wherein the at least one of the at least two cyclical behavior includes at least one of the following:
  a) sleep inertia;
  b) the homeostatic sleep need;
  c) the circadian sleep need;
  d) dream recall;
  e) reduction in sleep onset;
  f) best time and duration to nap;
  g) the best time to exercise;
  h) the best type of exercise;
  i) a healthier diet;
  j) increased productivity k) improved mood;
  l) the best time to take a medication;
  m) the best dosage of medication; or
  n) any combination thereof.

8. The medium of claim 1, wherein the behavioral feedback includes at least one of the following:
  a) an alarm set at a wake-time;
  b) at least one indication of when to go to sleep;
  c) suggestion of amount of sleep;
  d) when to exercise;
  e) how much to exercise;
  f) sleep instructions;
  g) workout instructions;
  h) medication instructions;
  i) diet instructions;
  j) a vigilance task; or
  k) any combination thereof.

9. The medium of claim 7, wherein the behavioral data includes at least one of the following:
  a) information relating to bedtime;
  b) wake time;
  c) at least one sleep quality survey;
  d) at least one sleep efficiency survey;
  e) at least one sleepiness survey;

f) severity of depression;
g) at least one habit survey;
h) at least one medication use survey;
i) invasively collected sample;
j) non-invasively collected sample;
k) a user's fitness level;
I) a user's diet habits;
m) a user's exercise habits; or
n) any combination thereof.

10. The medium of claim 1, wherein at least one of the at least two cyclical behavior[s] includes a behavior that co-varies with depression severity.

11. The medium of claim 10, further including identifying, from the behavioral data, at least one of the at least two cyclical behavior that co-varies with depression severity.

12. The medium of claim 1, wherein the at least one of the at least two cyclical behavior includes a behavior that co-varies with a fitness behavior.

13. The medium of claim 12, further including identifying at least one user-selected fitness behavior.

14. The medium of claim 7, wherein the at least one physiological factor includes at least one of the following:
    a) a homeostatic component;
    b) a circadian component;
    c) a sleep stage upon waking component;
    d) choronobiology;
    e) neurochemistry;
    f) physical cycles (need a better word for this: i.e. periods, food needs, menopause, etc.; or
    g) any combination thereof.

15. The medium of claim 1, wherein:
    a) each iterative process is performed within the at least one sampling window; and
    b) the size of the at least one sampling window is modified based upon changes in behavioral data.

16. The medium of claim 1, wherein at least one of the at least two cyclical behavior includes a behavior that co-varies with sleep interia.

* * * * *